(12) United States Patent
Hopkins et al.

(10) Patent No.: US 10,745,400 B2
(45) Date of Patent: Aug. 18, 2020

(54) INHIBITION OF BMP SIGNALING, COMPOUNDS, COMPOSITIONS AND USES THEREOF

(71) Applicant: Vanderbilt University, Nashville, TN (US)

(72) Inventors: Corey R. Hopkins, Bennington, NE (US); Matthew Ritter, San Diego, CA (US); Charles C. Hong, Nolensville, TN (US); Anish Vadukoot, Omaha, NE (US); Darren W. Engers, Brentwood, TN (US); Craig W. Lindsley, Brentwood, TN (US)

(73) Assignees: Vanderbuilt University, Nashville, TN (US); La Jolla Pharmaceuticals Company, San Diego, CA (US)

(*) Notice: Subject to any disclaimer, the term of this patent is extended or adjusted under 35 U.S.C. 154(b) by 0 days.

(21) Appl. No.: 16/353,745

(22) Filed: Mar. 14, 2019

(65) Prior Publication Data

US 2019/0284183 A1    Sep. 19, 2019

Related U.S. Application Data

(60) Provisional application No. 62/643,062, filed on Mar. 14, 2018.

(51) Int. Cl.
| | | |
|---|---|---|
| *C07D 471/10* | (2006.01) | |
| *A61K 31/438* | (2006.01) | |
| *C07D 471/04* | (2006.01) | |
| *A61P 35/00* | (2006.01) | |

(52) U.S. Cl.
CPC ............ *C07D 471/04* (2013.01); *A61P 35/00* (2018.01)

(58) Field of Classification Search
CPC .. C07D 471/10; C07D 471/02; C07D 401/14; A61K 31/438; A61K 31/437; A61K 31/496
USPC ........... 546/16, 121; 544/127, 362; 514/278, 514/300, 253
See application file for complete search history.

(56) References Cited

U.S. PATENT DOCUMENTS

| | | | |
|---|---|---|---|
| 4,810,705 A | 3/1989 | Bourguignon et al. | |
| 7,666,879 B2 | 2/2010 | Barda et al. | |
| 8,507,501 B2 | 8/2013 | Yu et al. | |
| 8,822,684 B1 | 9/2014 | Hong et al. | |
| 8,895,745 B2 * | 11/2014 | Berdini ................ | C07D 471/04 546/121 |
| 9,040,694 B1 | 5/2015 | Hong et al. | |
| 9,045,484 B2 | 6/2015 | Yu et al. | |
| 9,145,419 B2 | 9/2015 | Velaparthi et al. | |
| 9,738,636 B2 | 8/2017 | Hopkins et al. | |
| 10,196,392 B2 | 2/2019 | Hopkins et al. | |

| | | |
|---|---|---|
| 2010/0093760 A1 | 4/2010 | Yu et al. |
| 2010/0120761 A1 | 5/2010 | Berdini et al. |
| 2010/0210641 A1 | 8/2010 | Shaw et al. |
| 2011/0098471 A1 | 4/2011 | Katoh et al. |
| 2013/0029964 A1 | 1/2013 | Aoki et al. |

FOREIGN PATENT DOCUMENTS

| | | |
|---|---|---|
| JP | 47-047396 | 11/1972 |
| WO | 2001/038326 A2 | 5/2001 |
| WO | 2002/066480 A2 | 8/2002 |
| WO | 2003/092595 A2 | 11/2003 |
| WO | 2006/091671 A2 | 8/2006 |
| WO | 2008033408 A2 | 3/2008 |
| WO | 2008045393 A2 | 4/2008 |
| WO | 2008/078091 A1 | 7/2008 |
| WO | 2008/078100 A2 | 7/2008 |
| WO | WO2008078091 A1 | 7/2008 |
| WO | 2008107125 A1 | 9/2008 |
| WO | 2008121687 A2 | 10/2008 |
| WO | 2008124323 A1 | 10/2008 |
| WO | 2009002534 A1 | 12/2008 |
| WO | 2009/013335 A1 | 1/2009 |
| WO | 2009/050183 A2 | 4/2009 |
| WO | 2009/114180 A1 | 9/2009 |
| WO | 2009150240 A1 | 12/2009 |
| WO | 2009157423 A1 | 12/2009 |
| WO | 2010083145 A1 | 7/2010 |
| WO | 2010108074 A2 | 9/2010 |
| WO | 2010119285 A1 | 10/2010 |
| WO | 2011008640 A1 | 1/2011 |
| WO | 2011/136264 A1 | 11/2011 |
| WO | 2012088266 A2 | 6/2012 |
| WO | 2013/016452 A2 | 1/2013 |
| WO | WO2014051698 A1 | 4/2014 |
| WO | 2014/138088 A1 | 9/2014 |
| WO | 2014/160203 A2 | 10/2014 |

(Continued)

OTHER PUBLICATIONS

Aiguade et al., "Novel Triazolopyridylbenzamides as Potent and Selective p38a Inhibitors," Bioorg Med Chem Lett, 22: 3431-3436 (2012).

Alarmo et al., "Bone morphogenetic protein 7 is widely overexpressed in primary breast cancer," Genes, Chromosomes, and Cancer, 45(4): 411-419 (2006).

Bao et al., "BMP4, a strong better prognosis predictor, has a subtype preference and cell development association in gliomas," J Transl Med, 11(1):1-7 (2013).

Boyle et al., "Stem cell therapy for cardiac repair: ready for the next step," Circulation, 114(4): 339-352 (2006).

(Continued)

*Primary Examiner* — Charanjit Aulakh
(74) *Attorney, Agent, or Firm* — Stites & Harbison PLLC; Richard S. Myers, Jr.

(57) ABSTRACT

Provided herein are substituted imidazo[1,2-a]pyridines useful as inhibitors of BMP signaling. The invention further provides pharmaceutical compositions of the compounds of the invention. The invention also provides medical uses of substituted imidazo[1,2-a]pyridines.

17 Claims, No Drawings

(56) References Cited

FOREIGN PATENT DOCUMENTS

| WO | 2016130897 A1 | 8/2016 | |
|---|---|---|---|
| WO | WO 2018/053126 A1 * | 3/2018 | ........... C07D 471/04 |
| WO | WO2018053126 A1 | 3/2018 | |
| WO | WO2018136634 A1 | 7/2018 | |

OTHER PUBLICATIONS

Chen et al., "Developing and Applying a Gene Functional Association Network for Anti-angiogenic Kinase Inhibitor Activity Assessment in an Angiogenesis Co-Culture Model," BMC Genomics, 9: 1-16 (2008).

Cross et al., "Application of Small Organic Molecules Reveals Cooperative TGF ☐☐and BMP Regulation of Mesothelial Cell Behaviors," ACS Chem Biol, 6: 952-961 (2011).

Cuny et al., "Structure-activity relationship study of bone morphogenetic protein (BMP) signaling inhibitors," Bioorg Med Chem Lett, 18(15): 4388-4392 (2008).

Daniels et al., "Microwave-assisted protocols for the expedited synthesis of pyrazolo [1,5-a] and [3,4-d] pyrimidines," Tetrahedron Lett, 49(2): 305-310 (2008).

Fraenkel et al., "Ferroportin 1 is Required for Normal Iron Cycling in Zebrafish," J Clin Invest, 115(6): 1532-1541 (2005).

Fraley et al., "Optimization of pyrazolo [1,5-a]pyrimidine class of KDR kinase inhibitors: improvements in physical properties enhance cellular activity and pharmacokinetics," Bioorg Med Chem Lett, 12(24): 3537-3541 (2002).

Fraley et al., "Synthesis and initial SAR studies of 3,6-disubstituted pyrazolo[1,5-a]pyrimidines: a new class of KDR kinase inhibitors," Bioorg Med Chem Lett, 12(19): 2767-2770 (2002).

Hao et al., "Dorsomorphin, a selective small molecule inhibitor of BMP signaling, promotes cardiomyogenesis in embryonic stem cells," PLoS One, 3(8): e2904 (2008).

Hao et al., "In Vivo Structure-activity Relationship Study of Dorsomorphin Analogues Identifies Selective VEGF and BMP Inhibitors," ACS Chem Biol, 5(2): 245-253 (2010).

Hong et al., "Applications of small molecule BMP inhibitors in physiology and disease," Cytokines Growth Factor Rev, 20(5): 409-418 (2009).

Hong et al., "Cardiac induction by dorsomorphin, a selective small molecule inhibitor of BMP signaling," Circ Res, 103(5): e44 (2008).

Hong et al., "Large-scale small molecule screen using zebrafish embryos," Cell-Based Assays for High-Throughput Screening: Methods and Protocols, 43-55 (2009).

Hong et al., "Role of crosstalk between phosphatidylinositol 13-kinase and extracellular signal-regulated kinase pathways in artery-vein specification," Circ Res, 103(6): 573-579 (2008).

International Search Report and Written Opinion for International Application No. PCT/US2018/014239 dated Jun. 21, 2018.

International Search Report and Written Opinion for International Application No. PCT/US2019/022311 dated Jun. 18, 2019.

Kaplan et al., "Early mortality and cardiorespiratory failure in patients with fibrodysplasia ossificans progressiva," J Bone Joint Surg Am, 92(3): 686-691 (2010).

Kattman et al., "Multipotent Flk-1+ cardiovascular progenitor cells give rise to the cardiomyocyte, endothelial, and vascular smooth muscle lineages," Dev Cell, 11(5): 723-732 (2006).

Kim et al., "Decreased expression of bone morphogenetic protein (BMP) receptor type II correlates with insensitivity to BMP-6 in human renal cell carcinoma cells," Clin Cancer Res, 9(16): 6046-6051 (2003).

Langenfeld et al., "Bone morphogenetic protein 2 stimulation of tumor growth involves the activation of Smad-1/5," Oncogene, 25(5): 685-692 (2006).

Langenfeld et al., "Expression of bone morphogenetic proteins in human lung carcinomas," Ann Thorac Surg, 80(3): 1028-1032 (2005).

Mendez-Ferrer et al., "Resident progenitors and bone marrow stem cells in myocardial renewal and repair," Nat Clin Prac Cardiovascular Med, 3(1): S83-S89 (2006).

Nemeth et al., "Hepcidin Regulates Cellular Iron Efflux by Binding to Ferroportin and Inducing its Internalization," Science, 306(5704): 2090-2093 (2004).

Nicolas et al., "Constitutive Hepcidin Expression Prevents Iron Overload in a Mouse Model of Hemochromatosis," Nat Genet, 34(1): 97-101 (2003).

Nicolas et al., "Severe Iron Deficiency Anemia in Transgenic Mice Expressing Liver Hepcidin," Proc Natl Acad Sci USA, 99(7): 4596-4601 (2002).

Pigeon et al., "A New Mouse Liver-Specific Gene, Encoding a Protein Homologous to Human Antimicrobial Peptide Hepcidin, is Overexpressed During Iron Overload," J Biol Chem, 276(11): 7811-7819 (2001).

Squires et al., "Potent, Selective Inhibitors of Fibroblast Growth Factor Receptor Define Fibroblast Growth Factor Dependence in Preclinical Cancer Models," Mol Cancer Ther, 10(9): 1542-1552 (2011).

Wada et al., "Highly efficient differentiation and enrichment of spinal motor neurons derived from human and monkey embryonic stem cells," PLoS One, 4(8): e6722 (2009).

Waite et al., "From developmental disorder to heritable cancer: its all in the BMP/TGF-β family," Nat Rev Genet, 4(10): 763-773 (2003).

Wang et al., "Selective modulation of TLR4-activated inflammatory responses by altered iron homeostasis," J Clin Invest, 119(11): 3322-3328 (2009).

Wu et al., "Design and Synthesis of 1-5 3.7-diarylimidazopyridines as Inhibitors of the VEGF-receptor KDR," Bioorg Med Chem Lett, 14(4): 909-912 (Feb. 23, 2004).

Yu et al., "BMP type I receptor inhibition reduces heterotopic ossification," Nat Med, 14(12): 1363-1369 (2008).

Yu et al., "BMP type II receptor is required for BMP-mediated growth arrest and differentiation in pulmonary artery smooth muscle cells," J Biol Chem, 283(7): 3877-3888 (2008).

Yu et al., "Dorsomorphin inhibits BMP signals required for embryogenesis and iron metabolism," Nat Chem Biol, 4(1): 33-41 (2008).

Yurugi et al., "Studies on the Synthese of N-Heterocyclic Compounds XIV Syntheses of 7-Phenyl-s-triazolo(4,3-a} pyridine Derivatives," Yakugaku Zasshi, 93(5): 642-647 (1973).

* cited by examiner

INHIBITION OF BMP SIGNALING, COMPOUNDS, COMPOSITIONS AND USES THEREOF

RELATED APPLICATIONS

This application claims the benefit of priority to U.S. Provisional Patent Application Ser. No. 62/643,062, filed Mar. 14, 2018, which is hereby incorporated herein by reference in its entirety.

BACKGROUND

Signaling involving the Transforming Growth Factor β (TGF-β) superfamily of ligands is central to a wide range of cellular processes, including cell growth, differentiation, and apoptosis. TGF-β signaling involves binding of a TGF-β ligand to a type II receptor (a serine/threonine kinase), which recruits and phosphorylates a type I receptor. The type I receptor then phosphorylates a receptor-regulated SMAD (R-SMAD; e.g., SMAD1, SMAD2, SMAD3, SMAD5, SMAD8 or SMAD9), which binds to SMAD4, and the SMAD complex then enters the nucleus where it plays a role in transcriptional regulation. The TGF superfamily of ligands includes two major branches, characterized by TGF-β/activin/nodal and Bone Morphogenetic Proteins (BMPs).

Signals mediated by bone morphogenetic protein (BMP) ligands serve diverse roles throughout the life of vertebrates. During embryogenesis, the dorsoventral axis is established by BMP signaling gradients formed by the coordinated expression of ligands, receptors, co-receptors, and soluble antagonists. Excess BMP signaling causes ventralization, an expansion of ventral at the expense of dorsal structures, while diminished BMP signaling causes dorsalization, an expansion of dorsal at the expense of ventral structures. BMPs are key regulators of gastrulation, mesoderm induction, organogenesis, and endochondral bone formation, and regulate the fates of multipotent cell populations. BMP signals also play critical roles in physiology and disease, and are implicated, for example, in primary pulmonary hypertension, hereditary hemorrhagic telangiectasia syndrome, fibrodysplasia ossificans progressiva, and juvenile polyposis syndrome among others.

The BMP signaling family is a diverse subset of the TGF-β superfamily. Over twenty known BMP ligands are recognized by three distinct type II (BMPRII, ActRIIa, and ActRIIb) and at least three type I (ALK2, ALK3, and ALK6) receptors. Dimeric ligands facilitate assembly of receptor heteromers, allowing the constitutively-active type II receptor serine/threonine kinases to phosphorylate type I receptor serine/threonine kinases. Activated type I receptors phosphorylate BMP-responsive (BR-) SMAD effectors (SMADs 1, 5, and 8) to facilitate nuclear translocation in complex with SMAD4, a co-SMAD that also facilitates TGF signaling. In addition, BMP signals can activate intracellular effectors such as MAPK p38 in a SMAD-independent manner. Soluble BMP antagonists such as noggin, chordin, gremlin, and follistatin limit BMP signaling by ligand sequestration.

A role for BMP signals in regulating expression of hepcidin, a peptide hormone and central regulator of systemic iron balance, has also been suggested. Hepcidin binds and promotes degradation of ferroportin, the sole iron exporter in vertebrates. Loss of ferroportin activity prevents mobilization of iron to the bloodstream from intracellular stores in enterocytes, macrophages, and hepatocytes. The link between BMP signaling and iron metabolism represents a potential target for therapeutics.

Given the tremendous structural diversity of the BMP and TGF-β superfamily at the level of ligands (>25 distinct ligands at present) and receptors (three type I and three type II receptors that recognize BMPs), and the heterotetrameric manner of receptor binding, traditional approaches for inhibiting BMP signals via soluble receptors, endogenous inhibitors, or neutralizing antibodies are not practical or effective. Endogenous inhibitors such as noggin and follistatin have limited specificity for ligand subclasses. Single receptors have limited affinity for ligand, whereas ligand heterotetramers exhibit rather precise specificity for particular ligands. Neutralizing antibodies are specific for particular ligands or receptors and are also limited by the structural diversity of this signaling system.

Thus, there is a continuing need for pharmacologic agents that antagonize BMP signaling pathways and that can be used to manipulate these pathways in therapeutic or experimental applications.

SUMMARY OF INVENTION

In one aspect, the invention relates to compounds having the structure of Formula I or a pharmaceutically acceptable salt thereof:

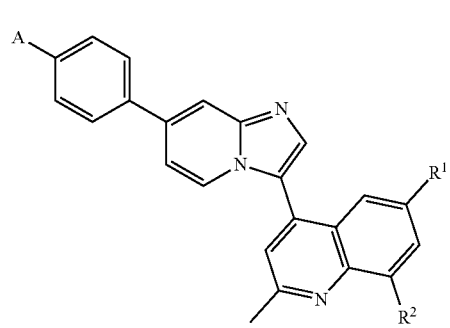

wherein $R^1$ and $R^2$ are each independently H or halo;

A is

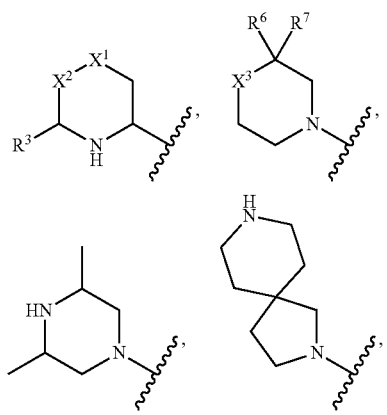

-continued

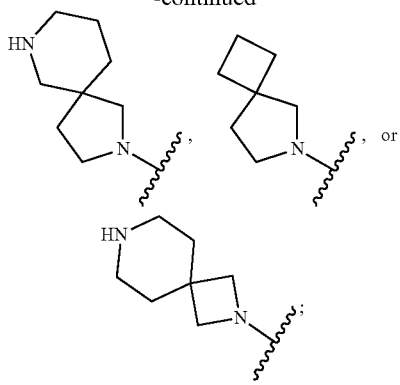

$X^1$ is O or NH;
$X^2$ is $CR^4R^5$ or $-CH_2CH_2-$;
$X^3$ is $CR^8R^9$ or NH;
$R^3$, $R^4$, and $R^5$ are each independently H or alkyl, or $R^4$ and $R^5$ combine to form an optionally substituted 4-, 5-, or 6-membered ring;
$R^6$ and $R^7$ are each independently H or alkyl, or $R^6$ and $R^7$ combine to form an optionally substituted 4-, 5-, or 6-membered ring; and
$R^8$ and $R^9$ are each independently H or alkyl, or $R^8$ and $R^9$ combine to form an optionally substituted 4-, 5-, or 6-membered ring.

In another aspect, the invention relates to compounds having the structure of Formula II or a pharmaceutically acceptable salt thereof:

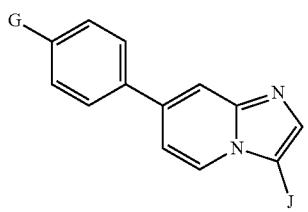

wherein
G is

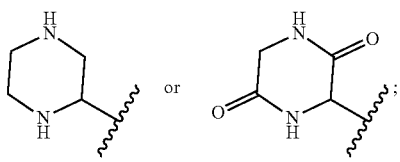

and
J is optionally substituted aryl or heteroaryl.

In yet another aspect, the invention relates to pharmaceutical compositions of a compound of Formula I and a pharmaceutically acceptable carrier.

The invention also relates to methods of treating or preventing a disease or condition comprising administering a compound or composition of the invention. In certain embodiments, the disease is cancer. The invention further relates to methods of inhibiting proliferation of a cancer cell, comprising contacting a cancer cell with a compound or composition of the invention.

The invention also relates to methods of modulating the BMP signaling pathway, comprising contacting a cell with a compound or composition of the invention.

The invention also provides methods for propagating, engrafting, or differentiating a progenitor cell, comprising contacting the cell with a compound or composition of the invention in an amount effective to propagate, engraft, or differentiate the progenitor cell.

DETAILED DESCRIPTION OF THE INVENTION

In certain aspects, the invention provides substituted imidazo[1,2-a]pyridine compounds, and pharmaceutical compositions thereof. In particular, such substituted compounds are useful as BMP inhibitors, and thus can be used to treat or prevent a disease or condition.

I. Compounds

In certain embodiments, the invention relates to compounds having the structure of Formula (I), or a pharmaceutically acceptable salt thereof:

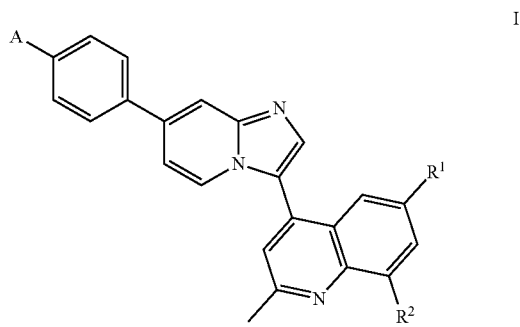

wherein
$R^1$ and $R^2$ are each independently H or halo;
A is

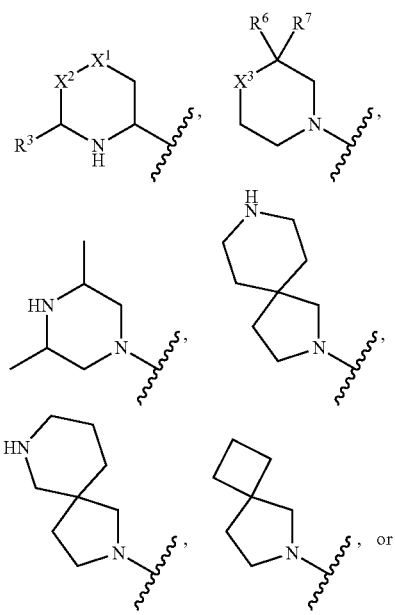

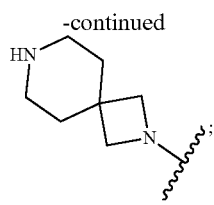

$X^1$ is O or NH;
$X^2$ is $CR^4R^5$ or —$CH_2CH_2$—;
$X^3$ is $CR^8R^9$ or NH;
$R^3$, $R^4$, and $R^5$ are each independently H or alkyl, or $R^4$ and $R^5$ combine to form an optionally substituted 4-, 5-, or 6-membered ring;
$R^6$ and $R^7$ are each independently H or alkyl, or $R^6$ and $R^7$ combine to form an optionally substituted 4-, 5-, or 6-membered ring; and
$R^8$ and $R^9$ are each independently H or alkyl, or $R^8$ and $R^9$ combine to form an optionally substituted 4-, 5-, or 6-membered ring.

In certain embodiments of Formula I, $R^1$ is F. In certain embodiments, $R^2$ is F. In certain embodiments, $X^1$ is O. In certain embodiments, $X^1$ is NH.

In some embodiments of Formula I, $X^2$ is $CR^4R^5$. In certain embodiments, $R^4$ is H and $R^5$ is alkyl. In certain such embodiments, $R^5$ is lower alkyl (e.g., methyl). In some embodiments of Formula I, $R^4$ and $R^5$ combine to form an optionally substituted 5 or 6-membered ring. In certain such embodiments, the optionally substituted 5 or 6-membered ring comprises a heteroatom (e.g., N). In other embodiments $X^2$ is —$CH_2CH_2$—.

In some embodiments of Formula I, A is

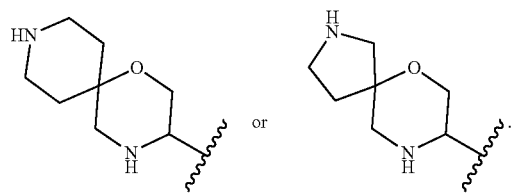 [SMILES: *C1COC2(CCNCC2)CN1 ; *C1COC2(CCNC2)CN1]

In some embodiments of Formula I, $X^3$ is NH. In some embodiments, $R^8$ and $R^9$ are each H.

In some embodiments of Formula, $R^6$ and $R^7$ are each lower alkyl (e.g., methyl). In other embodiments of Formula I, $R^6$ and $R^7$ combine to form an optionally substituted 4- or 5-membered ring. In some such embodiments, the optionally substituted 4 or 5-membered ring comprises a heteroatom (e.g., N).

In some embodiments of Formula I, A is

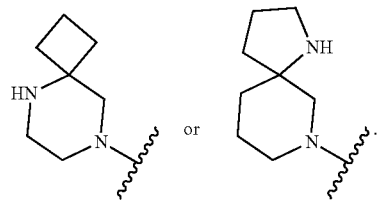 [SMILES: *N1CCNC2(CCC2)C1 ; *N1CCCC2(CCCN2)C1]

In some embodiments of Formula I, $R^8$ and $R^9$ combine to form an optionally substituted 4-, 5- or 6-membered ring. In some such embodiments, the optionally substituted 4 or 5-membered ring comprises a heteroatom (e.g., N)

In some embodiments of Formula I, A is

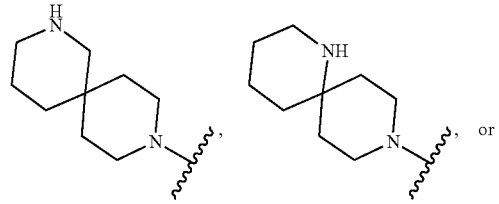

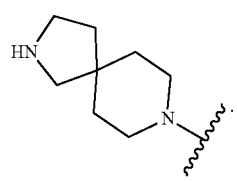

In some embodiments of Formula I, A is

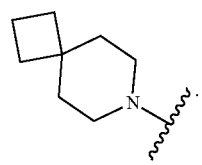 [SMILES: *N1CCC2(CCC2)CC1]

In another aspect, the invention relates to compounds having the structure of Formula II or a pharmaceutically acceptable salt thereof:

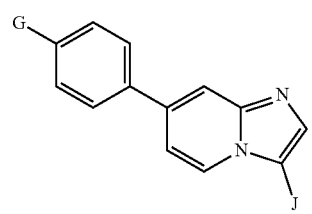

II wherein
G is

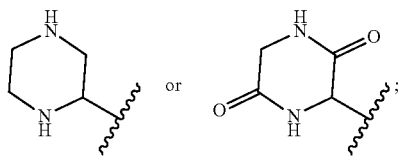 [SMILES: *C1CNCCN1 ; *C1NC(=O)CNC1=O]

and

J is optionally substituted aryl or heteroaryl.

In some embodiments of Formula II, G is

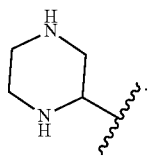 [SMILES: *C1CNCCN1]

In some embodiments of Formula II, J is heteroaryl. In some such embodiments, J is heteroaryl comprising a N heteroatom. In other embodiments, J is heteroaryl comprising N and S heteroatoms.

In some embodiments of Formula II, J is

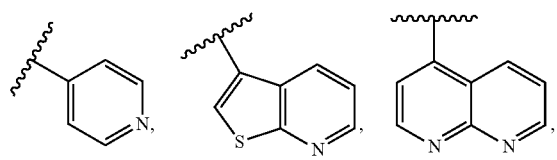

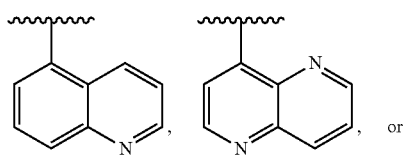, or

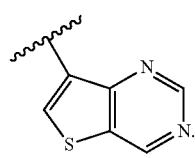

In some embodiments of Formula II, J is substituted aryl. In some such embodiments, J is aryl substituted with sulfonamide (e.g., naphthyl substituted with sulfonamide).

In some embodiments of Formula II, J is

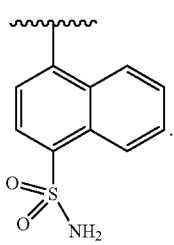 [SMILES: *c1ccc(S(N)(=O)=O)c2ccccc12]

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee, or even 95% or greater ee. The compounds of the invention have more than one stereocenter. Consequently, compounds of the invention may be enriched in one or more diastereomer. For example, a compound of the invention may have greater than 30% de, 40% de, 50% de, 60% de, 70% de, 80% de, 90% de, or even 95% or greater de.

In certain embodiments, as will be described in detail below, the present invention relates to methods of treating or preventing a disease or condition with a compound of Formula I or II, or a pharmaceutically acceptable salt thereof. In certain embodiments, the therapeutic preparation may be enriched to provide predominantly one enantiomer of a compound of Formula I or II. An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, the therapeutic preparation may be enriched to provide predominantly one diastereomer of a compound of Formula I or II. A diastereomerically enriched mixture may comprise, for example, at least 60 mol percent of one diastereomer, or more preferably at least 75, 90, 95, or even 99 mol percent.

In certain embodiments, the present invention provides a pharmaceutical preparation suitable for use in a human patient in the treatment of a disease or condition, comprising an effective amount of any compound of Formula I, and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for use in a human patient.

Compounds of any of the above structures may be used in the manufacture of medicaments for the treatment of any diseases or conditions disclosed herein.

Exemplary compounds disclosed herein (e.g., compounds of Formula I, compounds of Formula II) are depicted in Tables 1 and 2. The compounds of Tables 1 and 2 are understood to encompass both the free base and the conjugate acid. For example, the compounds in Table 1 may be depicted as complexes or salts with trifluoroacetic acid or hydrochloric acid, but the compounds in their corresponding free base forms or as salts with other acids are equally within the scope of the invention. Compounds may be isolated in either the free base form, as a salt (e.g., a hydrochloride salt) or in both forms. In the chemical structures shown below, standard chemical abbreviations are sometimes used.

TABLE 1

Exemplary Compounds

| Compound | Compound Number |
|---|---|
| (structure) | 1 |
| (structure) | 2 |
| (structure) | 3 |

TABLE 1-continued
Exemplary Compounds
| Compound | Compound Number |
|---|---|
| 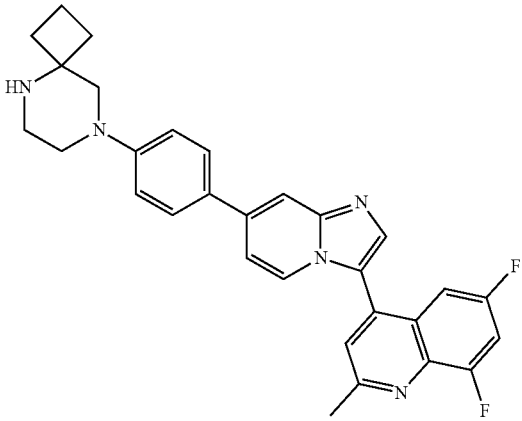 [SMILES: Cc1cc(-c2cnc3cc(-c4ccc(N5CCNC6(CCC6)C5)cc4)ccn23)c2cc(F)cc(F)c2n1] | 4 |
| 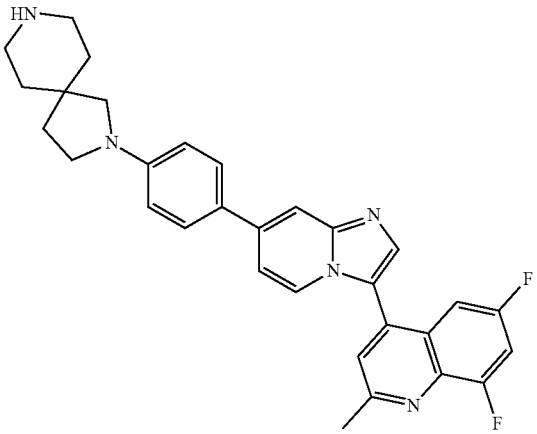 [SMILES: Cc1cc(-c2cnc3cc(-c4ccc(N5CCC6(CCNCC6)C5)cc4)ccn23)c2cc(F)cc(F)c2n1] | 5 |
| 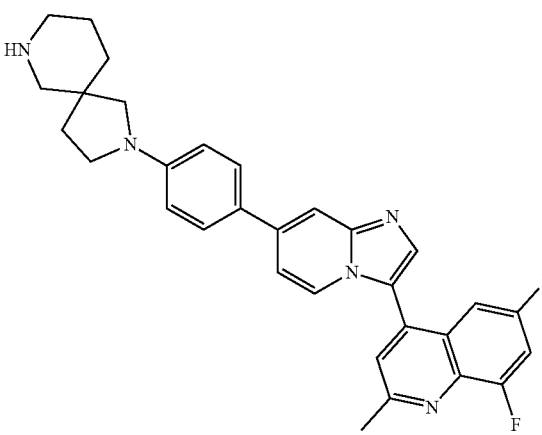 | 6 |

TABLE 1-continued
Exemplary Compounds
| Compound | Compound Number |
|---|---|
| 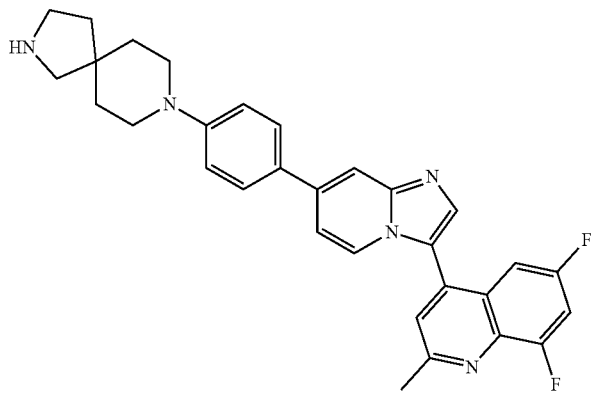 [SMILES: Cc1cc(-c2cnc3cc(-c4ccc(N5CCC6(CCNC6)CC5)cc4)ccn23)c2cc(F)cc(F)c2n1] | 7 |
| 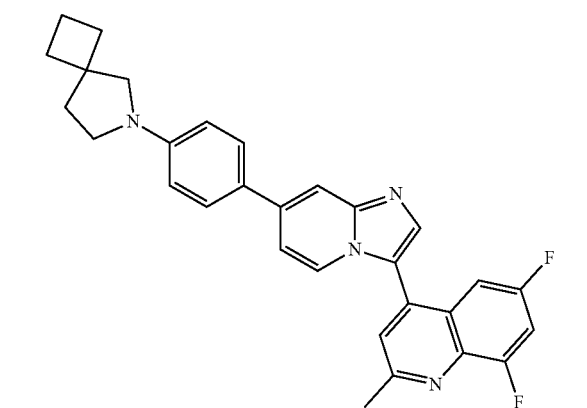 [SMILES: Cc1cc(-c2cnc3cc(-c4ccc(N5CCC6(CCC6)C5)cc4)ccn23)c2cc(F)cc(F)c2n1] | 8 |
| 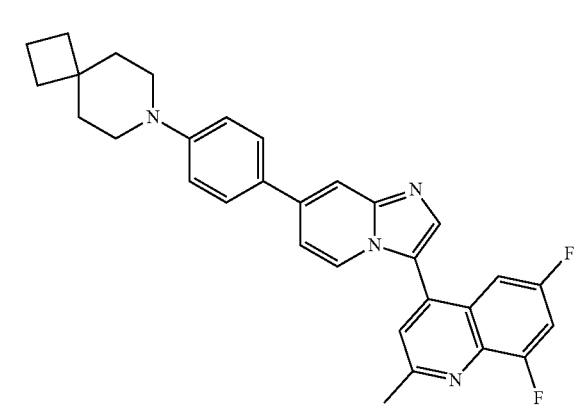 [SMILES: Cc1cc(-c2cnc3cc(-c4ccc(N5CCC6(CCC6)CC5)cc4)ccn23)c2cc(F)cc(F)c2n1] | 9 |

TABLE 1-continued
Exemplary Compounds
| Compound | Compound Number |
|---|---|
| 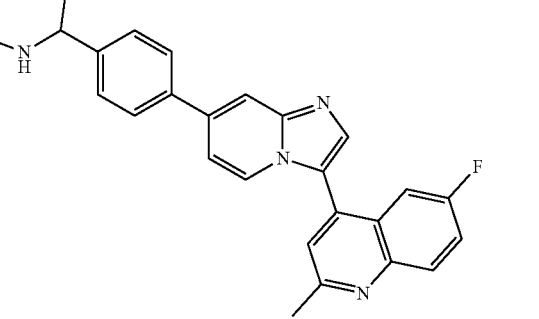 | 10 |
| 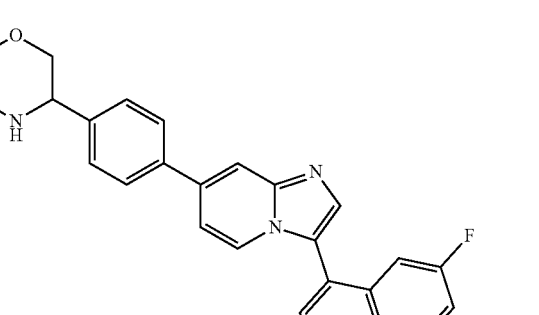 | 11 |
| 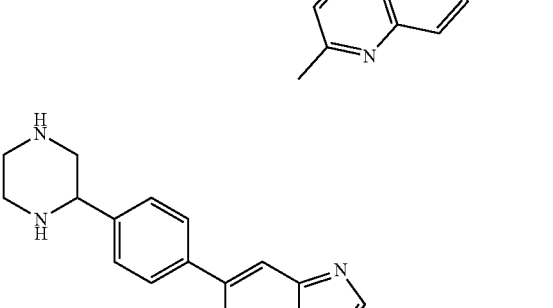 | 12 |
| 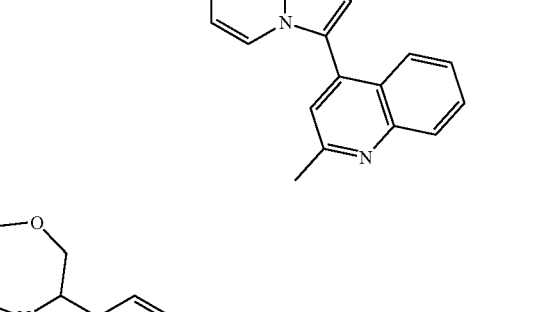 | 13 |

TABLE 1-continued

Exemplary Compounds

| Compound | Compound Number |
|---|---|
| | 14 |
| | 15 |
| | 16 |
| | 17 |

TABLE 1-continued
Exemplary Compounds
| Compound | Compound Number |
|---|---|
| 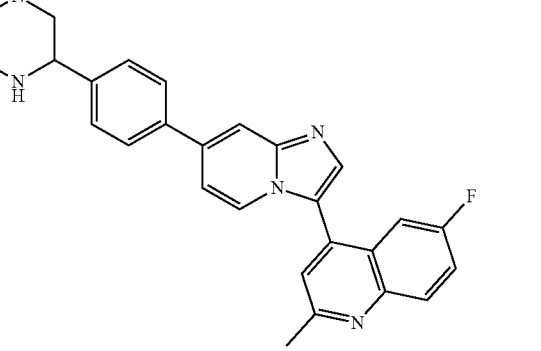 | 18 |
| 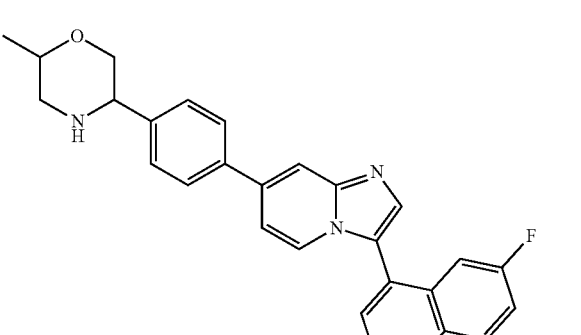 | 19 |
| 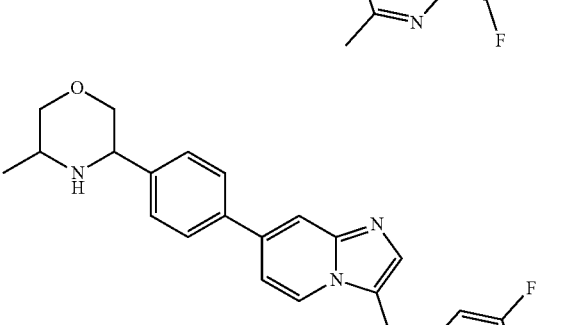 | 20 |
| 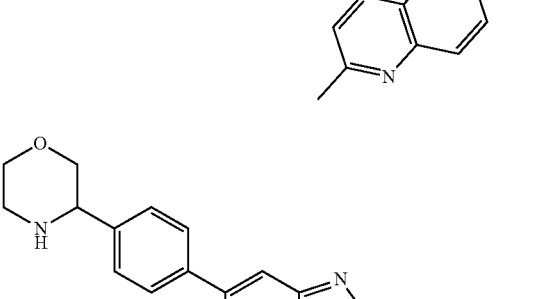 | 21 |

TABLE 1-continued

| Compound | Compound Number |
|---|---|
| (structure) | 22 |
| (structure) | 23 |
| (structure) | 24 |
| (structure) | 25 |

TABLE 1-continued
Exemplary Compounds
| Compound | Compound Number |
|---|---|
| 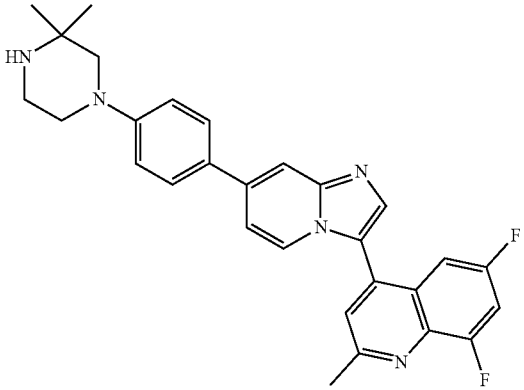 [SMILES: Cc1cc(-c2cnc3cc(-c4ccc(N5CCNC(C)(C)C5)cc4)ccn23)c2cc(F)cc(F)c2n1] | 26 |
| 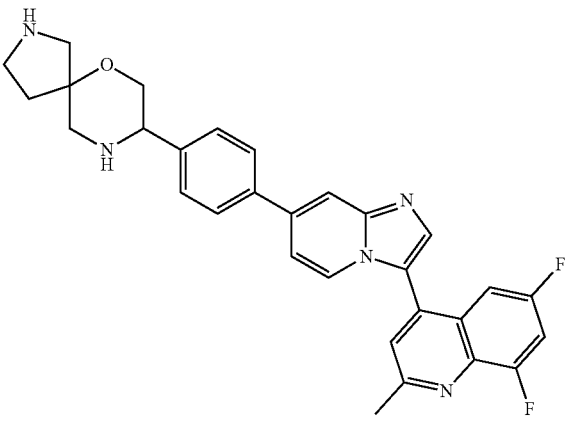 [SMILES: Cc1cc(-c2cnc3cc(-c4ccc(C5COC6(CCNC6)CN5)cc4)ccn23)c2cc(F)cc(F)c2n1] | 27 |
| 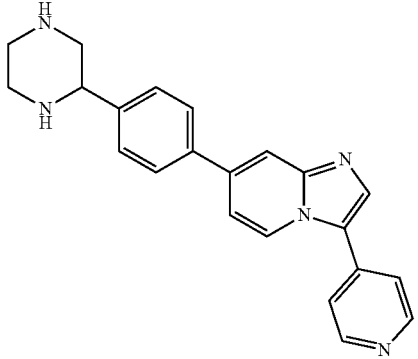 [SMILES: c1cc(-c2cnc3cc(-c4ccc(C5CNCCN5)cc4)ccn23)ccn1] | 30 |
| 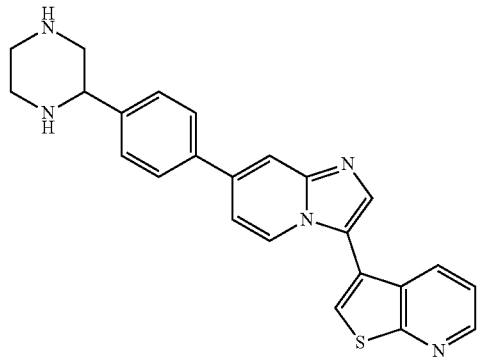 [SMILES: c1cnc2scc(-c3cnc4cc(-c5ccc(C6CNCCN6)cc5)ccn34)c2c1] | 31 |

TABLE 1-continued

Exemplary Compounds

| Compound | Compound Number |
|---|---|
| | 32 |
| | 33 |
| | 34 |
| | 35 |

TABLE 1-continued
Exemplary Compounds
| Compound | Compound Number |
|---|---|
| 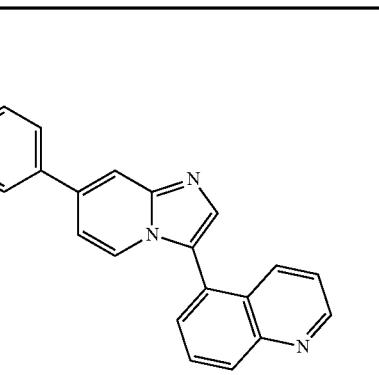 | 36 |
| 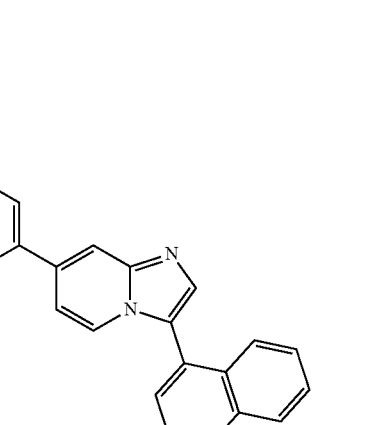 | 37 |
TABLE 2
Other exemplary compounds
| Compound | Compound Number |
|---|---|
| 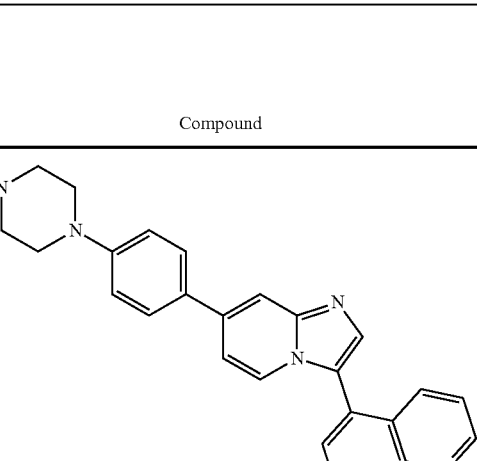 | 28 |
TABLE 2-continued
Other exemplary compounds
| Compound | Compound Number |
|---|---|
| | 29 |

TABLE 2-continued

Other exemplary compounds

| Compound | Compound Number |
|---|---|
| 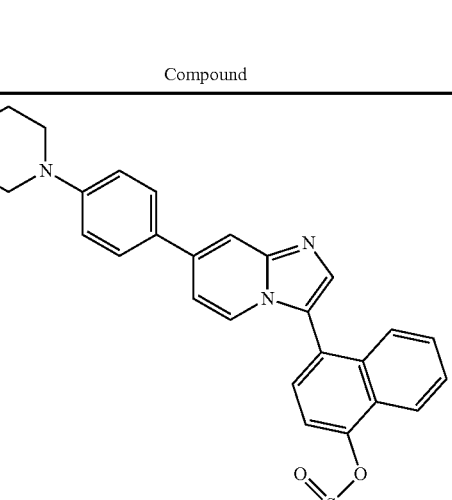 | 38 |

II. Pharmaceutical Compositions

In certain embodiments, the present invention provides pharmaceutical compositions comprising a compound of Formula I or a compound of Table 2 and a pharmaceutically acceptable carrier.

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

This invention includes the use of pharmaceutically acceptable salts of compounds of the invention in the compositions and methods of the present invention. The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I or Table 2. As another example, the salt may comprise less than one inorganic or organic acid molecule per molecule of base, such as two molecules of compound of Formula I or Table 2 per molecule of tartaric acid.

In further embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

III. Uses of Compounds and Compositions

In certain aspects, the invention provides methods of treating or preventing a disease or condition, comprising administering to a subject a compound of Formula I or Formula II or a compound of Table 2, in a therapeutically effective amount or a composition comprising a compound of Formula I or Formula II or a compound of Table 2.

In some embodiments, the disease is cancer. In some embodiments, the cancer is colorectal cancer, juvenile polyposis syndrome, sporadic colorectal cancer, leukemia, acute myeloid leukemia, acute megakaryoblastic leukemia (AMKL), non-Down syndrome AMKL, Down syndrome AMKL, chronic myelogenous leukemia, lung cancer, non-small cell lung cancer (NSCLC), pancreatic cancer, ovarian cancer, serous ovarian cancer, epithelial ovarian cancer, osteosarcomas, prostate cancer, bone cancer, renal cell cancer, breast cancer, melanoma, or head and neck squamous cell carcinoma (HNSCC).

In some embodiments, the cancer is a cancer of the central nervous system. In some embodiments, the cancer is a glioma, astrocytic glioma, diffuse intrinsic pontine glioma (DIPG), high grade glioma (HGG), germ cell tumor, glioblastoma multiform (GBM), oligodendroglioma, pituitary tumor, or ependymoma.

In certain embodiments, the cancer is a solid tumor. The subject is generally one who has been diagnosed as having a cancerous tumor or one who has been previously treated for a cancerous tumor (e.g., where the tumor has been previously removed by surgery). The cancerous tumor may be a primary tumor and/or a secondary (e.g., metastatic) tumor.

In certain embodiments, the subject is a mammal, e.g., a human.

In some embodiments, the disease is anemia, iron-refractory iron-deficient anemia (IRIDA), iron deficiency anemia, anemia of chronic disease, heterotopic ossification, nonhereditary myositis ossificans, myositis ossificans traumatica, myositis ossificans circumscripta, fibrodysplasia ossificans progressiva (FOP), inflammation, pathologic bone function, ectopic or maladaptive bone formation, a skin disease, hypertension, ventricular hypertrophy, atherosclerosis, spinal cord injury and neuropathy, heart disease, heart damage, liver damage, or liver disease.

In some embodiments, the liver disease is fatty liver disease, nonalcoholic fatty liver disease (NAFLD), nonalcoholic steatohepatitis (NASH), cirrhosis or liver failure.

In certain embodiments, the invention provides methods of inhibiting proliferation of a cancerous cell comprising contacting a cancerous cell with an effective amount of a compound of Formula I or Formula II or a compound of Table 2.

The invention also provides methods of inhibiting proliferation of a cancer cell, comprising contacting a cancer cell with a compound of Formula I or Formula II or Table 2 or a composition comprising a compound of Formula I or Formula II or a compound of Table 2.

The invention also provides method for propagating, engrafting, or differentiating a progenitor cell, comprising contacting the cell with a compound of Formula I or Formula II or a compound of Table 2 or a composition comprising a compound of Formula I or Formula II or a compound of Table 2 in an amount effective to propagate, engraft, or differentiate the progenitor cell.

The invention also provides methods of modulating the BMP signaling pathway in a cell, comprising contacting a cell with a compound of Formula I or Formula II or a compound of Table 2. Such methods may be performed in vivo or in vitro.

IV. Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, —OCF$_3$, ethoxy, propoxy, tert-butoxy and the like.

The term "cycloalkyloxy" refers to a cycloakyl group having an oxygen attached thereto.

The term "alkoxyalkyl" refers to an alkyl group substituted with an alkoxy group and may be represented by the general formula alkyl-O-alkyl.

The term "alkylaminoalkyl" refers to an alkyl group substituted with an alkylamino group.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

The term "$C_{x-y}$" when used in conjunction with a chemical moiety, such as acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS-.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

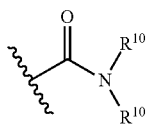

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

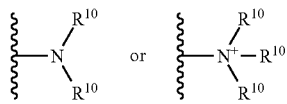

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

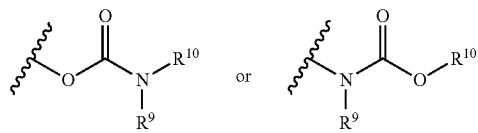

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0] hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group $-OCO_2R^{10}$, wherein $R^{10}$ represents a hydrocarbyl group.

The term "carboxy", as used herein, refers to a group represented by the formula $-CO_2H$.

The term "ester", as used herein, refers to a group $-C(O)OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The term "heteroalkylamino", as used herein, refers to an amino group substituted with a heteralkyl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, benzimidazole, quinoline, isoquinoline, quinoxaline, quinazoline, indole, isoindole, indazole, benzoxazole, pyrazine, pyridazine, purine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like. Heterocyclyl groups can also be substituted by oxo groups. For example, "heterocyclyl" encompasses both pyrrolidine and pyrrolidinone.

The term "heterocycloalkyl", as used herein, refers to an alkyl group substituted with a heterocycle group.

The term "heterocycloalkylamino", as used herein refers to an amino group substituted with a heterocycloalkyl group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

As used herein, the term "oxo" refers to a carbonyl group. When an oxo substituent occurs on an otherwise saturated group, such as with an oxo-substituted cycloalkyl group (e.g., 3-oxo-cyclobutyl), the substituted group is still intended to be a saturated group. When a group is referred to as being substituted by an "oxo" group, this can mean that a carbonyl moiety (i.e., —C(=O)—) replaces a methylene unit (i.e., —CH$_2$—).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

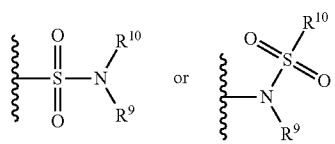

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group $-S(O)-R^{10}$, wherein $R^{10}$ represents a hydrocarbyl.

The term "sulfonate" is art-recognized and refers to the group $SO_3H$, or a pharmaceutically acceptable salt thereof.

The term "sulfone" is art-recognized and refers to the group $-S(O)_2-R^{10}$, wherein $R^{10}$ represents a hydrocarbyl.

The term "thioalkyl", as used herein, refers to an alkyl group substituted with a thiol group.

The term "thioester", as used herein, refers to a group $-C(O)SR^{10}$ or $-SC(O)R^{10}$ wherein $R^{10}$ represents a hydrocarbyl.

The term "thioether", as used herein, is equivalent to an ether, wherein the oxygen is replaced with a sulfur.

The term "urea" is art-recognized and may be represented by the general formula

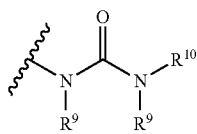

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3rd Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of formula I). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

EXAMPLES

Examples of compounds disclosed herein (e.g., of Formula I) or pharmaceutically acceptable salts thereof having useful biological activity are listed above in Table 1 and Table 2.

Example 1: Chemical Syntheses

The general procedures used in the methods to prepare the compounds of the present invention are analogous to those described in International Application No. PCT/US2013/032588, incorporated by reference in its entirety, and specifically with respect to the methods of preparing the compounds disclosed therein.

Scheme 1. Exemplary synthesis of carbon linked compounds
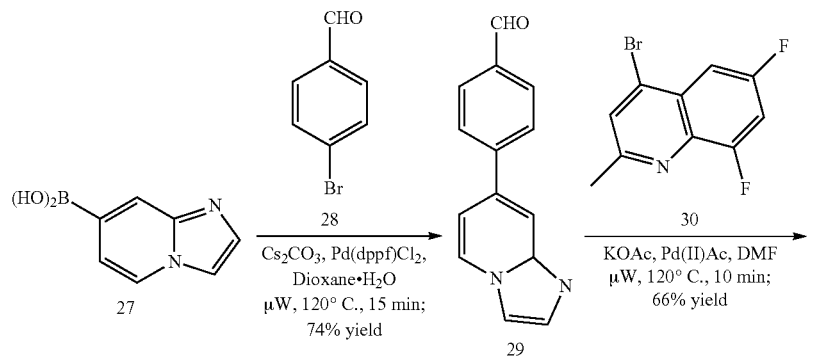
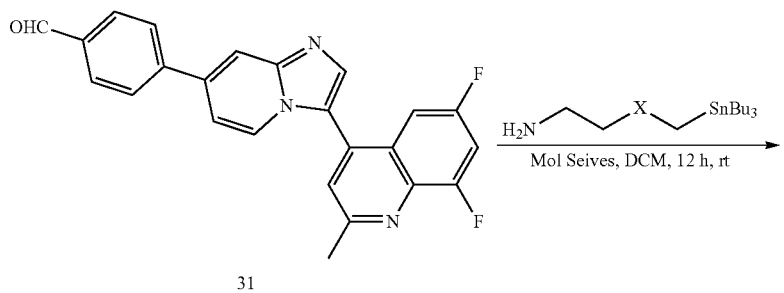
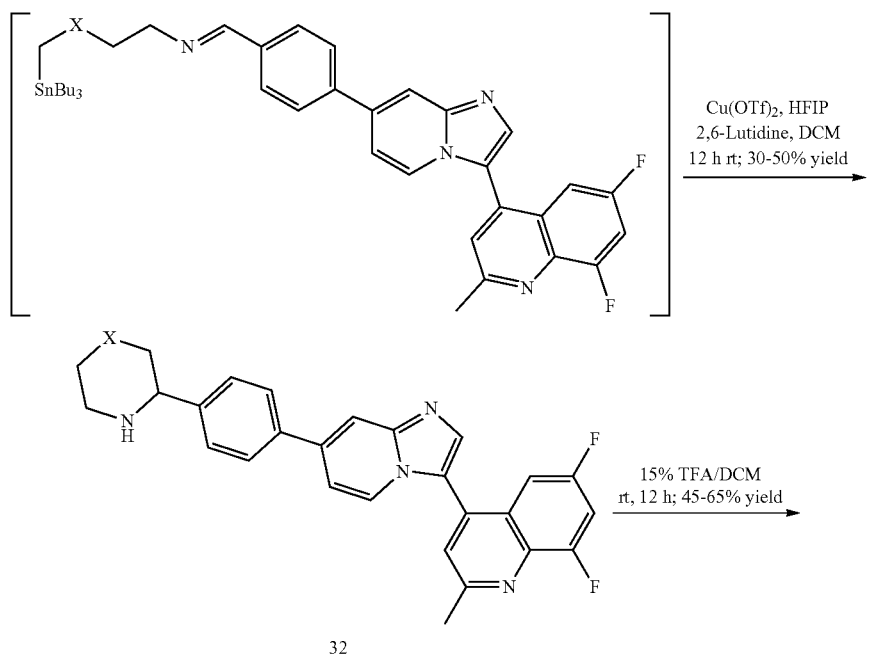

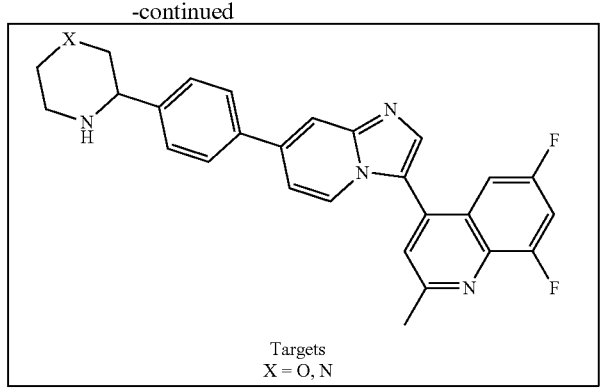

Targets
X = O, N

For example, certain compounds disclosed are synthesized according to the protocol as outlined in Scheme 1. Briefly, starting with commercially available intermediate 27 which was subjected to palladium-catalyzed cross-coupling under Suzuki conditions with intermediate 28 to yield the aldehyde intermediate 29 in good yield. Another direct coupling reaction with the bromoquinoline intermediate 30 and intermediate 29 enabled the penultimate intermediate 31 to be made efficiently. A variety of bromine coupling partners (such as intermediate 28) could be used which would expand the scope of this synthetic procedure. The SLAP chemistry was performed with the commercially available tin (Sn) reagents which first reacted with the aldehyde giving the imine, which was directly reacted with Cu(OTf)$_2$ to cyclize into intermediate 32. The available tin reagents allowed for the synthesis of piperazine and morpholine analogs. The piperazine analogs were then synthesized by deprotection of a Boc group.

Scheme 2-Synthesis of compounds 37 and 38.

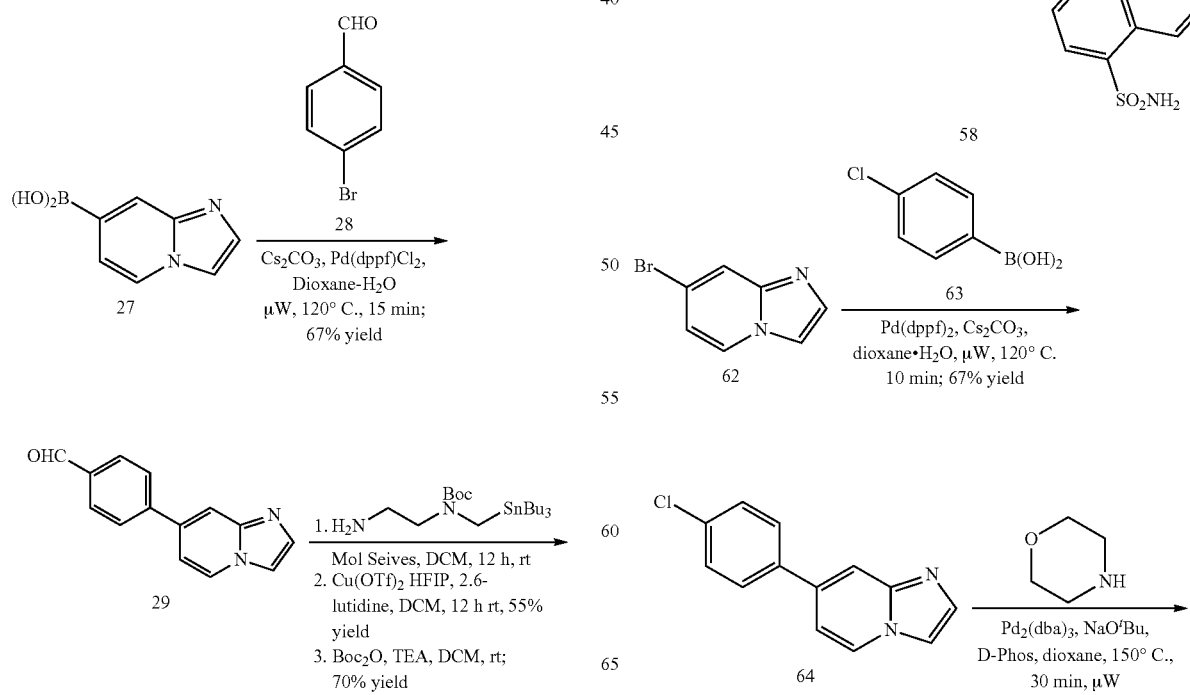

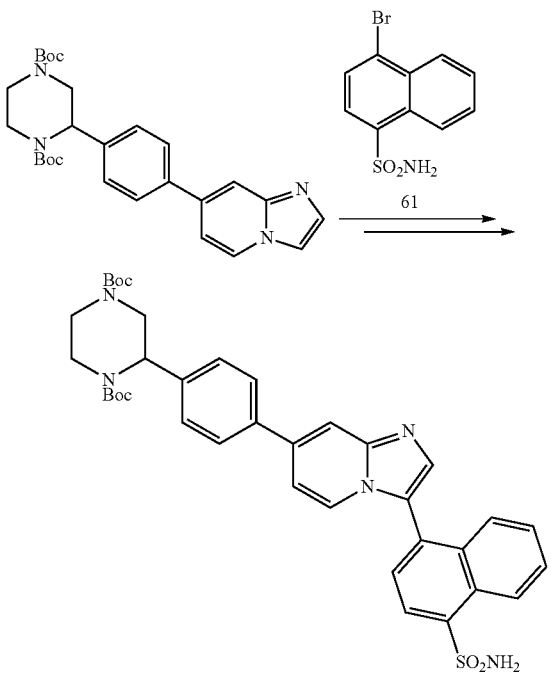

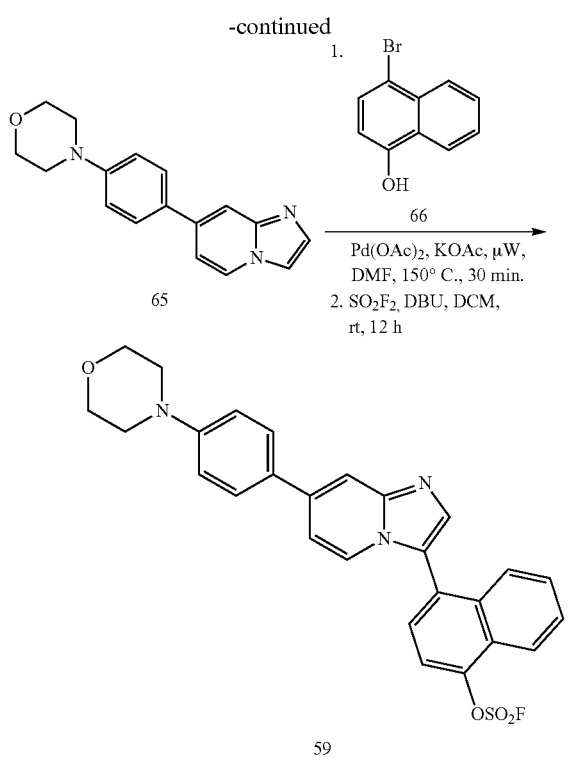

The synthesis of compounds 37 and 38 is shown in Scheme 2. Briefly, sulfonamide, intermediate 58, was synthesized starting from the imidazo[1,2-a]pyridin-7-ylboronic acid, intermediate 27, which underwent palladium-catalyzed cross-coupling with intermediate 28 to yield intermediate 29. Next, SLAP chemistry was used to yield the mono-Boc protected piperazine which was further protected with Boc$_2$O to give the bis-Boc protected piperazine, intermediate 60. The desired final compound was synthesized by cross-coupling with the bromonaphthalene, intermediate 61, via known procedures followed by Boc-deprotection. Compound 38 was synthesized as outlined in Scheme 2. 7-Bromoimidazo[1,2-a]pyridine, intermediate 62, was reacted with intermediate 63 under palladium catalysis to yield intermediate 64. Next, morpholine was reacted under Buchwald cross-coupling conditions to yield intermediate 65. The final target 59 (compound 38) was then realized by cross-coupling reaction with 4-bromonaphthalen-1-ol, intermediate 66, which was then subjected to SO$_2$F$_2$ to give the final target 59 (compound 38).

Example 2: Biological Assays

Table 3-9 summarize the results of assays used to identify and evaluate embodiments of the present invention.

The kinase assays were carried out briefly as follows. Substrate was prepared in Base Reaction Buffer (20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO). The indicated kinases was delivered into the substrate solution and allowed to gently mix. Next, the specific compound was delivered in DMSO into the kinase mixture by Acoustic technology (Echo550; nanoliter range), and allowed to incubate for 20 minutes at room temperature. Next, $^{33}$P-ATP was delivered into the reaction mixture to initiate the reaction and allowed to incubate at room temperature. After 2 hours, the reactions were spotted onto P81 ion exchange paper and the kinase activity is detected by the filter-binding method.

The BMP4 cell assay were carried out briefly as follows. Stably transfected BMP-responsive C2C12 mouse myoblast cells (containing the Id1 promoter-firefly luciferase reporter) were seeded in 96-well plates and incubated overnight with the compounds and BMP4 (50 ng/mL). The cells were then lysed, and cell extracts were then subjected to the firefly luciferase assay using Steady-Glo luciferase assay kit (Promega). The results were normalized to cell titers, as measured using Cell Titer-Glo luminescence assay (Promega). For subtype analysis, C2C12BRA cells were transiently transfected with plasmids (0.1 µg) expressing constitutively active forms of the BMP type I receptors (caALK2, caALK3 or caALK6) using Lipofectamine kit (Invitrogen) in 96 well plates; 0.1 µg of pRL-TK *Renilla* luciferase (Promega) was used to control for transfection efficiency. Relative activity was quantified by the ratio of firefly to *Renilla* luciferase activities using the dual luciferase assay kit (Promega).

TABLE 3

| Kinase Selectivity Data for selected compounds (nM) | | | | | | | | | |
|---|---|---|---|---|---|---|---|---|---|
| Compound Number | 1 | 2 | 3 | 4 | 5 | 6 | 7 | 8 | 9 |
| ALK1/ACVRL1 (100 mM) | 880 | 936 | 10300 | 386 | | 35300 | 3460 | 5950 | >50,000 | >50,000 |
| ALK2/ACVR1 (20 mM) | 54.2 | 147 | 1090 | 29 | 2370 | 171 | 770 | >50,000 | >50,000 |
| ALK2 (Q207D, 20 mM) | 68.1 | 114 | 999 | 24 | 1740 | 200 | 745 | >50,000 | >50,000 |
| ALK2 (R206H, 20 mM) | 60.9 | 128 | 1120 | 25.5 | 2510 | 218 | 1070 | >50,000 | >50,000 |
| ALK3/BMPR1A (1 mM) | 28.5 | 45 | 332 | 2.52 | 1330 | 19.9 | 434 | 43700 | 40900 |

TABLE 4

| In Vitro Data and Kinase Selectivity Data for selected compounds | | |
|---|---|---|
| Compound Number | 28 | 29 |
| Primary In Vitro Data | | |
| BMP4 Cell Assay (nM) | 66 | 112 |
| caALK2 (nM) | 44 | 16 |
| caALK1 (nM) | 189 | 178 |
| FOP-ALK2 (nM) | | |

TABLE 4-continued

In Vitro Data and Kinase Selectivity Data for selected compounds

| Compound Number | 28 | 29 |
|---|---|---|
| Kinase Selectivity (nM) | | |
| ALK1/ACVRL1 (100 mM) | 1,200 | 767 |
| ALK2/ACVR1 (20 mM) | 114 | 84.9 |
| ALK2 (Q207D, 20 mM) | 79.1 | 77.6 |
| ALK2 (R206H, 20 mM) | 105 | 88.2 |
| ALK3/BMPR1A (1 mM) | <5.08 | 17.4 |

TABLE 5

Biological Assay data for selected compounds

| Compound number | 10 | 11 | 12 | 13 | 14 | 15 | 16 | 17 | 18 |
|---|---|---|---|---|---|---|---|---|---|
| Kinase Selectivity (nM) | | | | | | | | | |
| ALK1/ACVRL1 (100 mM) | <5.1 | 23.5 | <5.1 | 16.0 | <5.1 | 34.1 | 151.7 | 89.2 | 16.4 |
| ALK2/ACVR1 (20 mM) | <5.1 | <5.1 | <5.1 | <5.1 | <5.1 | <5.1 | <5.1 | <5.1 | <5.1 |
| ALK2 (Q207D, 20 mM) | <5.1 | <5.1 | <5.1 | <5.1 | <5.1 | <5.1 | 6.3 | <5.1 | <5.1 |
| ALK2 (R206H, 20 mM) | <5.1 | <5.1 | <5.1 | <5.1 | <5.1 | <5.1 | <5.1 | <5.1 | <5.1 |
| ALK3/BMPR1A (1 mM) | <5.1 | <5.1 | <5.1 | <5.1 | <5.1 | <5.1 | <5.1 | <5.1 | <5.1 |
| Intrinsic Clearance (mL/kg/min) | | | | | | | | | |
| Human (CL-Hep) | 138.78 (17.4) | 134.14 (17.4) | <23.13 (<10.7) | 97.15 (16.6) | 92.98 (16.5) | 74.02 (15.7) | <23.13 (<10.7) | 46.72 (14.0) | 32.84 (12.4) |
| Mouse (CL-Hep) | 100.98 (47.59) | 99.99 (47.37) | <49.5 (<32.94) | <49.5 (<32.94) | 113.85 (50.26) | 66.33 (38.13) | <49.5 (<32.94) | <49.5 (<32.94) | <49.5 (<32.94) |
| Protein Binding (% Free) | | | | | | | | | |
| Human | 2.39 | 1.52 | 13.6 | 1.85 | 0.76 | 1.26 | 5.61 | 10.3 | 7.33 |
| Mouse | 1.91 | 3.23 | 4.94 | 2.3 | 1.6 | 1.01 | 4.7 | 8.52 | 5.48 |

TABLE 6

Biological Assay data for selected compounds

| Compound number | 19 | 20 | 21 | 22 | 23 | 24 | 25 | 26 | 27 |
|---|---|---|---|---|---|---|---|---|---|
| Kinase Selectivity (nM) | | | | | | | | | |
| ALK1/ACVRL1 (100 mM) | 14.1 | 23.0 | <5.1 | 72.1 | 42.8 | 1252.0 | 777.0 | 330.0 | 907.0 |
| ALK2/ACVR1 (20 mM) | <5.1 | <5.1 | <5.1 | 5.6 | <5.1 | 57.8 | 55.5 | 14.9 | 29.1 |
| ALK2 (Q207D, 20 mM) | <5.1 | <5.1 | <5.1 | 12.7 | <5.1 | 129.0 | 170.0 | 69.7 | 219.0 |
| ALK2 (R206H, 20 mM) | <5.1 | <5.1 | <5.1 | 7.1 | <5.1 | 58.3 | 258.0 | 79.3 | 326.0 |
| ALK3/BMPR1A (1 mM) | <5.1 | <5.1 | <5.1 | <5.1 | <5.1 | 5.2 | 54.7 | 5.7 | 13.5 |
| Intrinsic Clearance (mL/kg/min) | | | | | | | | | |
| Human (CL-Hep) | 77.25 (15.9) | 117.04 (17.1) | 138.78 (17.5) | 138.78 (17.5) | 138.78 (17.5) | 46.26 (14.0) | 46.26 (14.0) | <23.13 (<10.7) | <23.13 (<10.7) |
| Mouse (CL-Hep) | 130.68 (53.30) | 113.64 (50.22) | 198 (97.79) | 97.13 (47.71) | 82.19 (42.92) | <49.5 (<32.94) | 198 (97.79) | 99 (47.14) | <49.5 (<32.94) |
| Protein Binding (% Free) | | | | | | | | | |
| Human | 3.74 | 4.01 | 3.05 | 1.94 | 1.11 | 0.75 | 1.43 | 0.61 | 4.97 |
| Mouse | 3.15 | 1.36 | 6.24 | 4.69 | 2.85 | 1.08 | 0.55 | 1.03 | 3.9 |

TABLE 7

Biological Assay data for selected compounds

| Compound Number | 12 | 16 | 17 | 18 | 27 | 22 | 23 |
|---|---|---|---|---|---|---|---|
| Kinase Selectivity (nM) | | | | | | | |
| ALK4 | 192 | 775 | 390 | 386 | 2,030 | 113 | 164 |
| ALK5 | 310 | 1,140 | 717 | 456 | 3,290 | 232 | 354 |
| ALK6 | 54.5 | 188 | 188 | 231 | 429 | 128 | 369 |
| BMPR2 | 54,400 | >100,000 | >100,000 | >100,000 | >100,000 | >50,000 | >100,000 |
| TGFbR2 | 4,590 | 620 | 498 | 2,680 | 1,870 | 388 | 560 |
| AMPK | 20,000 | 39,100 | 11,500 | 9,320 | 18,900 | 6,170 | >100,000 |
| KDR | 9,350 | 39,300 | 36,900 | 31,400 | >100,000 | 39,300 | 47,400 |
| PDGFRb | 2,820 | 7,700 | 6,930 | 6,490 | 21,700 | 5,200 | 7,340 |
| Cell Assay (nM) | | | | | | | |
| BMP4 | 13.5 | 87.7 | 29.6 | 34.9 | 248.3 | | |

TABLE 8

Biological Assay data for selected compounds

| Compound number | 30 | 31 | 32 | 33 | 34 | 35 | 36 | 37 | 38 |
|---|---|---|---|---|---|---|---|---|---|
| Kinase Selectivity (nM) | | | | | | | | | |
| ALK1/ACVRL1 (100 mM) | 447.0 | 30.7 | 197.0 | 61.3 | 16.9 | 14200.0 | 84.9 | 723.0 | >30,000 |
| ALK2/ACVR1 (20 mM) | 68.8 | 20.1 | 16.5 | <5.1 | 6.2 | 157.0 | <5.1 | 14.6 | >30,000 |
| ALK2 (Q207D, 20 mM) | 35.0 | <5.1 | <5.1 | <5.1 | <5.1 | 65.8 | <5.1 | 5.8 | 10300.0 |
| ALK2 (R206H, 20 mM) | 96.7 | 20.6 | 15.8 | <5.1 | 7.5 | 214.0 | <5.1 | 13.2 | 15000.0 |
| ALK3/BMPR1A (1 mM) | 55.1 | 21.2 | <5.1 | 82.7 | <5.1 | 9450.0 | 295.0 | 20300.0 | 23100.0 |
| Intrinsic Clearance (mL/kg/min) | | | | | | | | | |
| Human (CL-Hep) | | <23.1 (<11) | <23.1 (<11) | <23.1 (<11) | 29.6 (12.3) | | | <23.1 (<11) | |
| Mouse (CL-Hep) | | 53.5 (33.6) | <49.5 (<31.9) | <49.5 (<31.9) | <49.5 (<31.9) | | | <49.5 (<31.9) | |
| Protein Binding (% Free) | | | | | | | | | |
| Human | | 16.2 | 42.8 | 11 | 39.4 | | | 11.7 | |
| Mouse | | 6.8 | 33.9 | 8.4 | 21.2 | | | | |

TABLE 9

Biological Assay data for selected compounds

| | Compound Number | | | |
|---|---|---|---|---|
| | 32 | 33 | 36 | 37 |
| Kinase Selectivity (nM) | | | | |
| ALK4 | 192 | 775 | 390 | 386 |
| ALK5 | 310 | 1,140 | 717 | 456 |
| ALK6 | 54.5 | 188 | 188 | 231 |
| BMPR2 | 54,400 | >100,000 | >100,000 | >100,000 |
| TGFbR2 | 4,590 | 620 | 498 | 2,680 |
| AMPK | 20,000 | 39,100 | 11,500 | 9,320 |
| KDR | 9,350 | 39,300 | 36,900 | 31,400 |
| PDGFRb | 2,820 | 7,700 | 6,930 | 6,490 |
| Cell Assay (nM) | | | | |
| BMP4 | 13.5 | 87.7 | 29.6 | 34.9 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A compound having a structure of Formula I or a pharmaceutically acceptable salt thereof:

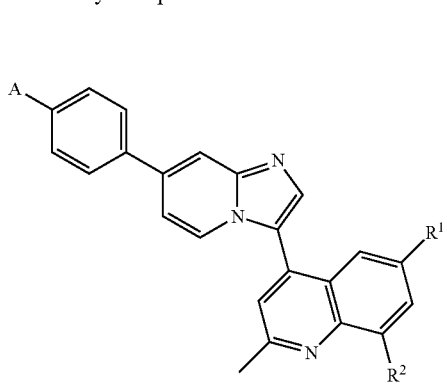

I wherein
R¹ and R² are each independently H or halo;
A is

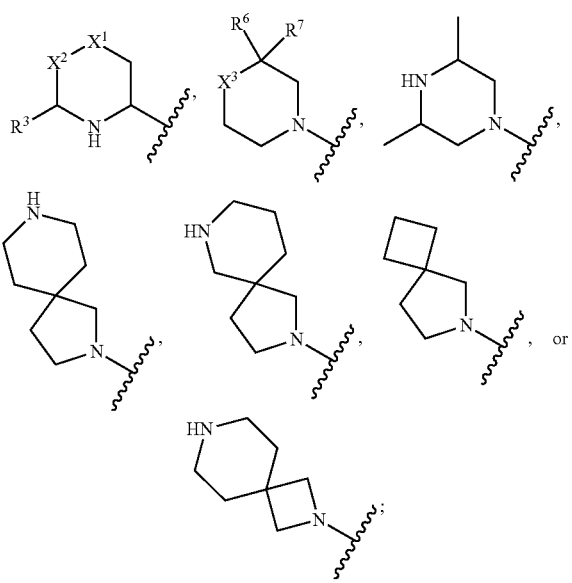

$X^1$ is O or NH;
$X^2$ is $CR^4R^5$ or —$CH_2CH_2$—;
$X^3$ is $CR^8R^9$ or NH;
$R^3$, $R^4$, and $R^5$ are each independently H or alkyl, or $R^4$ and $R^5$ combine to form an optionally substituted 4-, 5-, or 6-membered ring;
$R^6$ and $R^7$ combine to form an optionally substituted 4-, 5-, or 6-membered ring; and
$R^8$ and $R^9$ are each independently H or alkyl, or $R^8$ and $R^9$ combine to form an optionally substituted 4-, 5-, or 6-membered ring.

2. The compound of claim 1, wherein $R^1$ is F and $R^2$ is F.
3. The compound of claim 1, wherein $X^1$ is O.
4. The compound of claim 1, wherein $X^1$ is NH.
5. The compound of claim 1, wherein $R^4$ and $R^5$ combine to form an optionally substituted 5 or 6-membered ring.
6. The compound of claim 1, wherein $X^3$ is NH.
7. The compound of claim 1, wherein $R^6$ and $R^7$ combine to form an optionally substituted 4- or 5-membered ring.
8. The compound of claim 1, wherein $R^8$ and $R^9$ combine to form an optionally substituted 4-, 5- or 6-membered ring.

9. The compound of claim 1, wherein A is

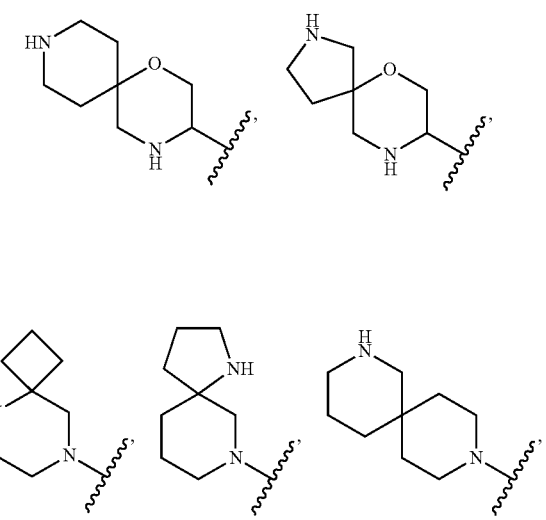

10. A compound having the structure of Formula II or a pharmaceutically acceptable salt thereof:

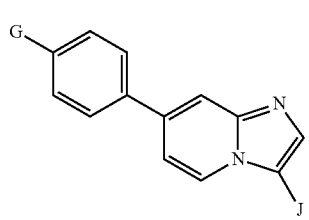

II wherein
G is

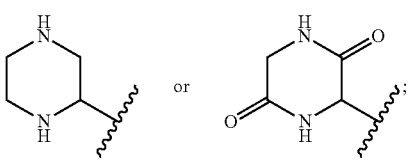 [SMILES: *C1CNCCN1 ; *C1NC(=O)CNC1=O]

and
J is selected from optionally substituted heteroaryl or
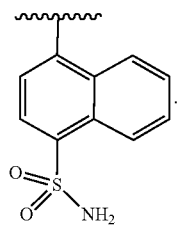 [SMILES: *c1ccc(S(N)(=O)=O)c2ccccc12]
11. The compound of claim 10, wherein G is
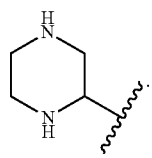 [SMILES: *C1CNCCN1]
12. The compound of claim 10, wherein J is
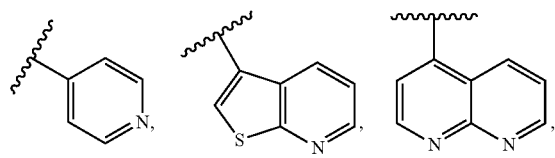
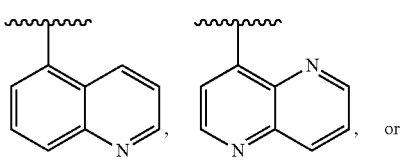
13. The compound of claim 10, wherein J is
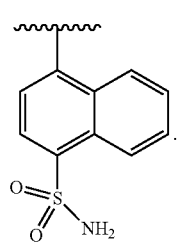
14. A compound selected from:
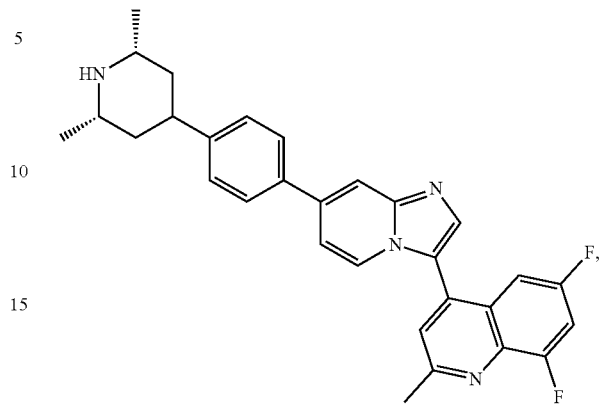
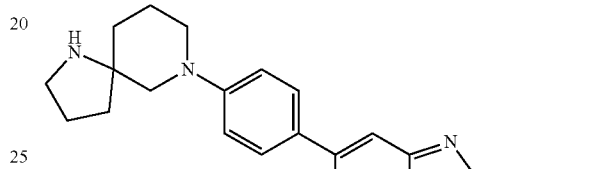
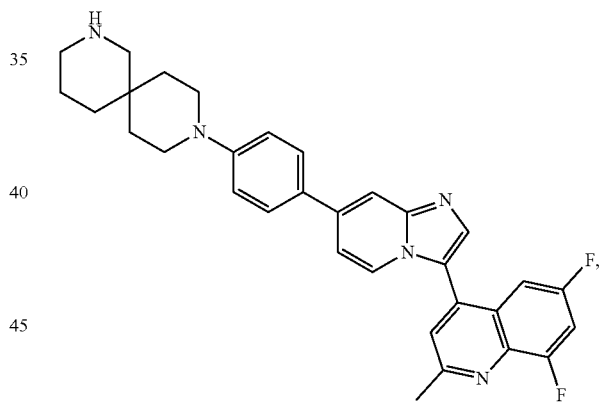
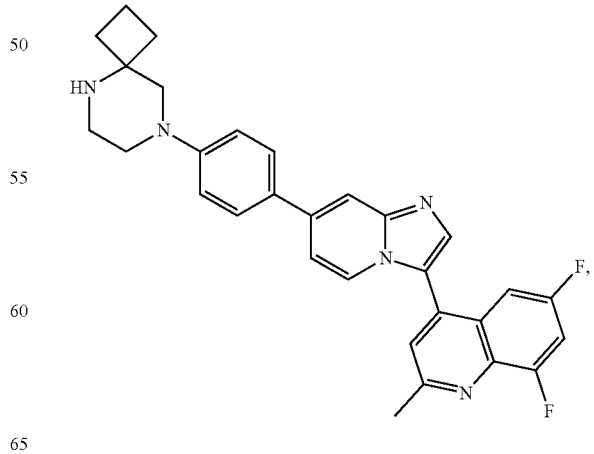

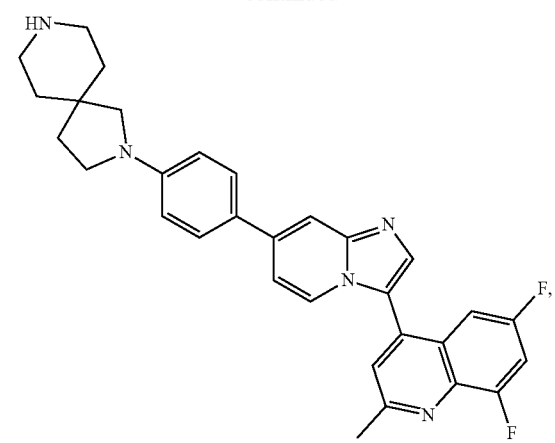
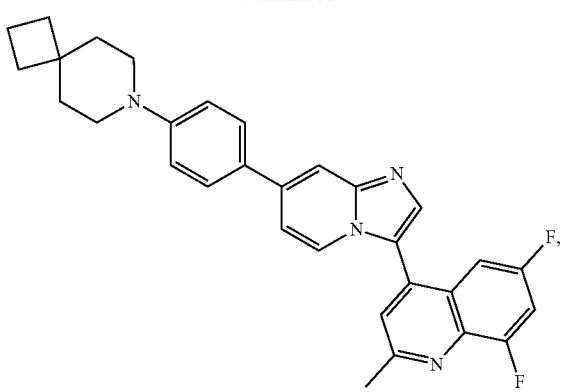
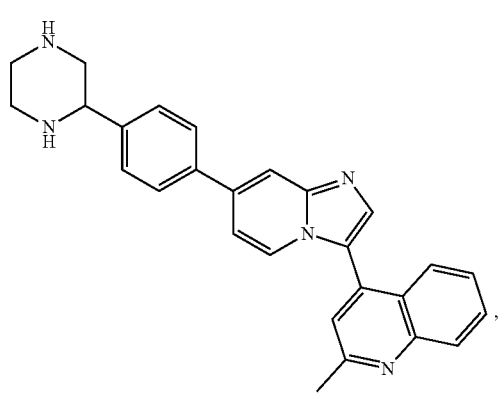

61
-continued
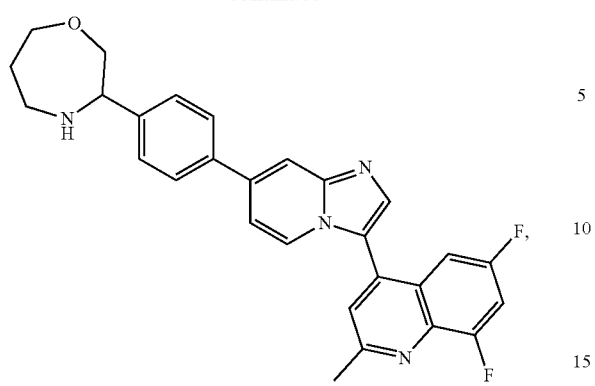
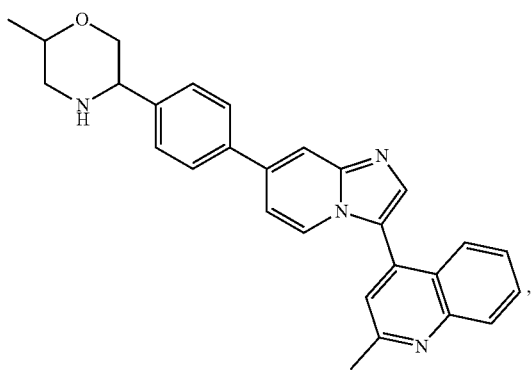
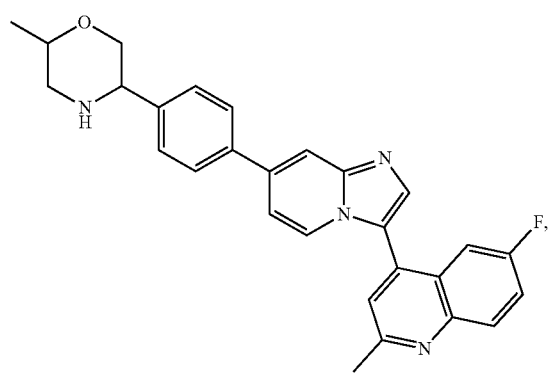
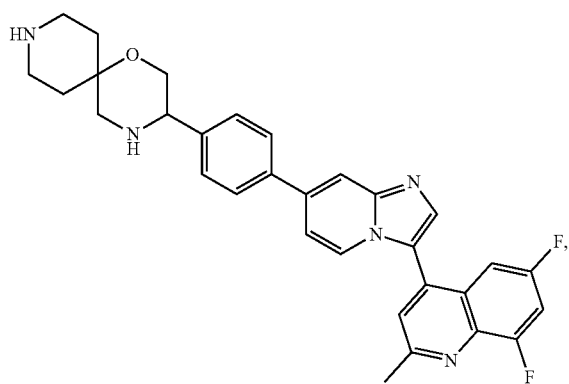
62
-continued
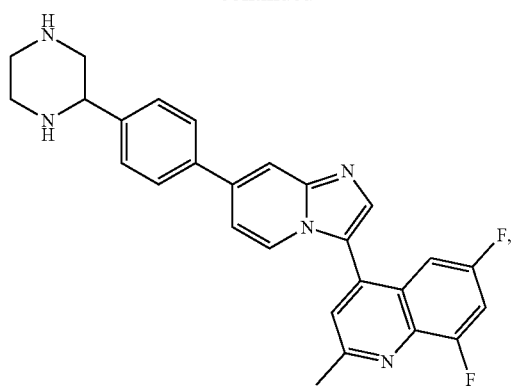
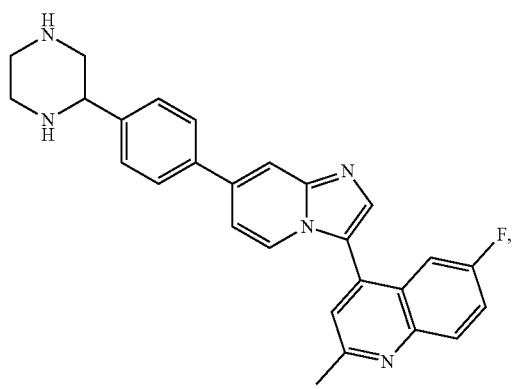
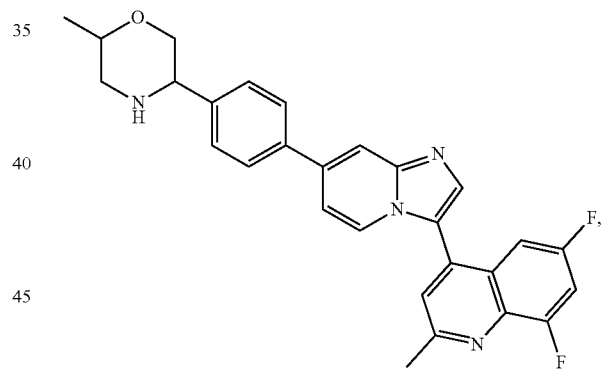
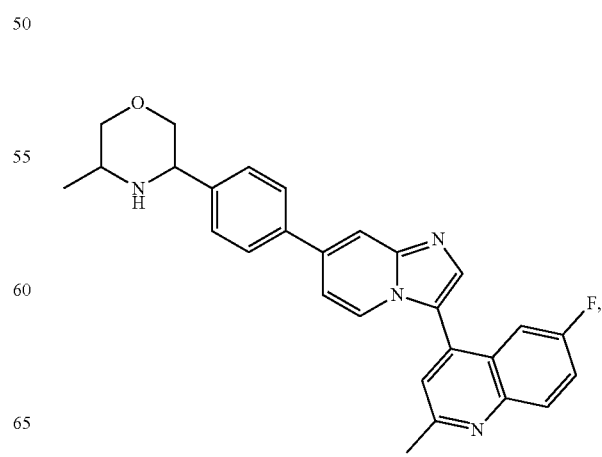

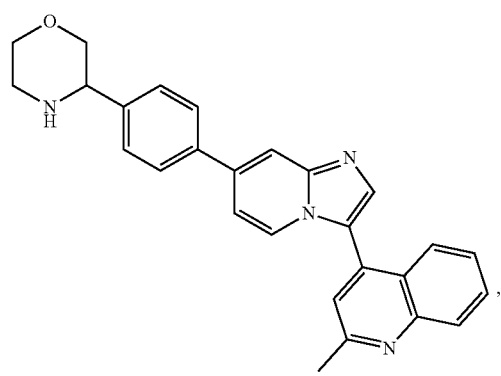
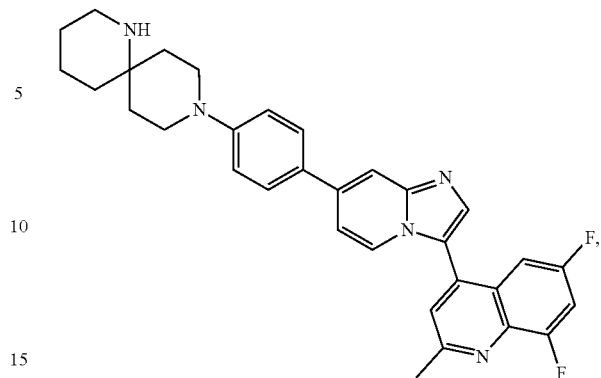
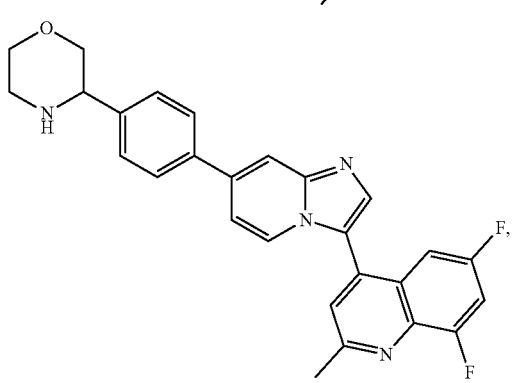
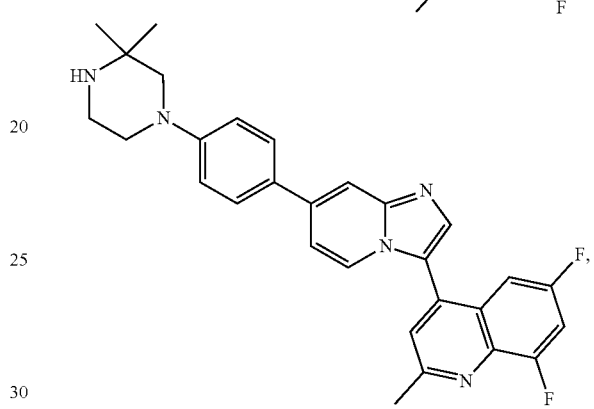
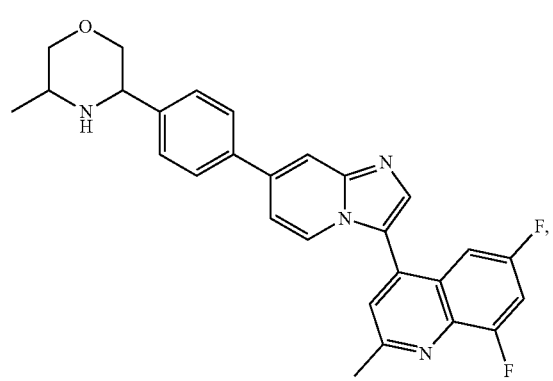
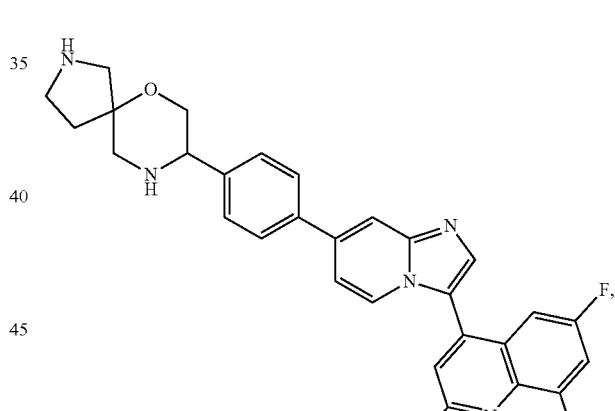
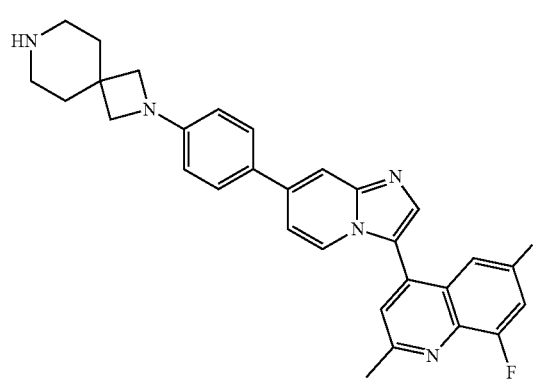
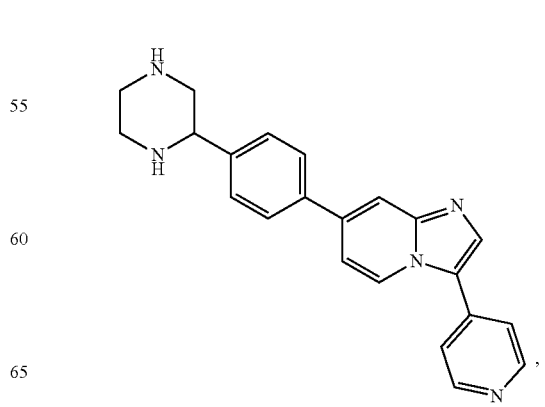

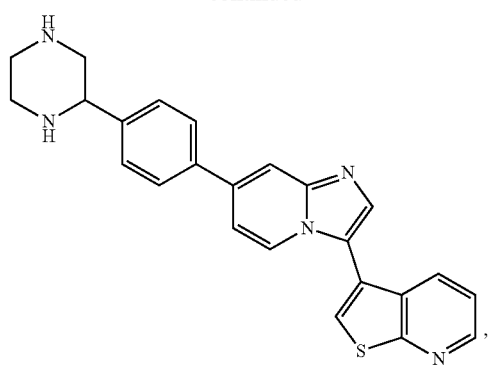
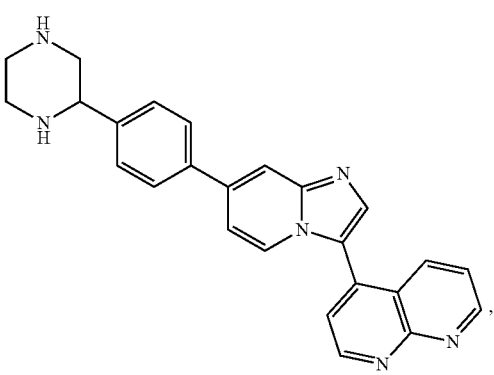
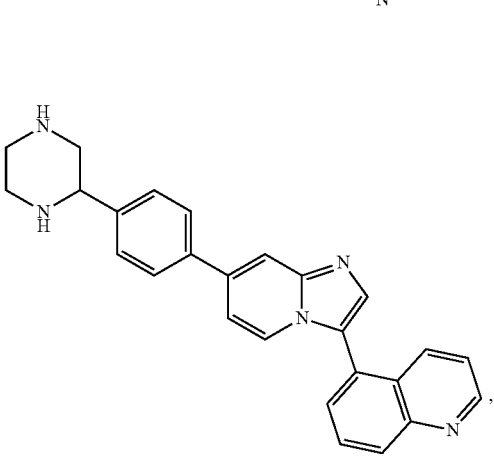
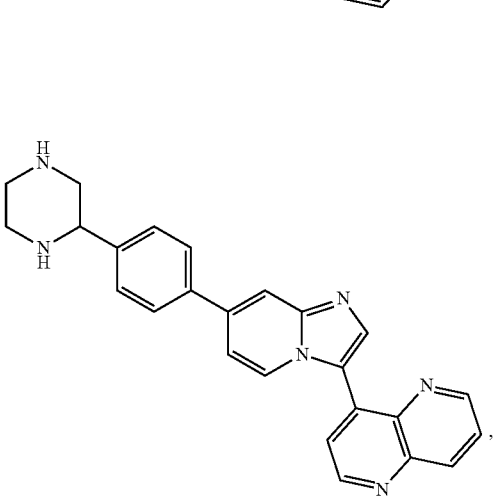
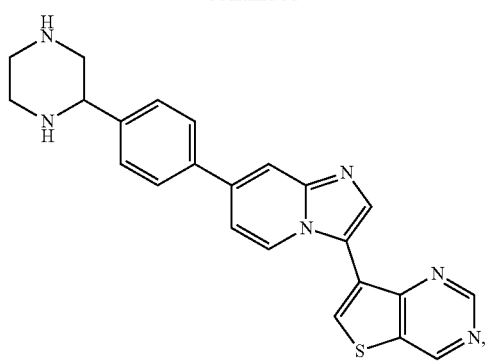
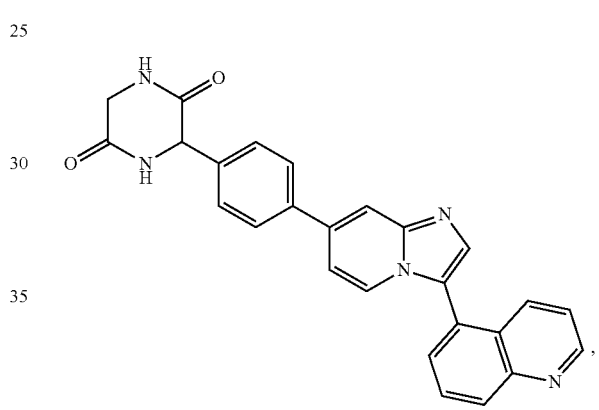
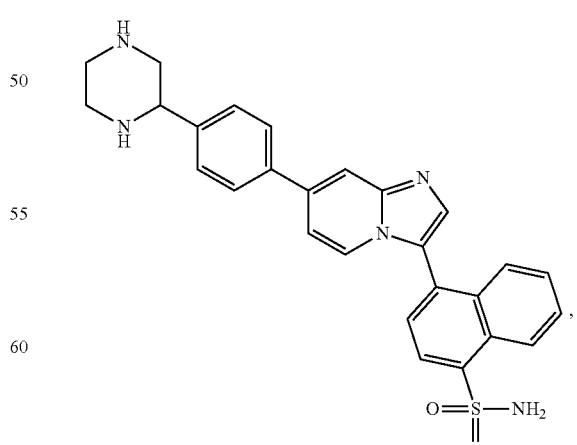

-continued

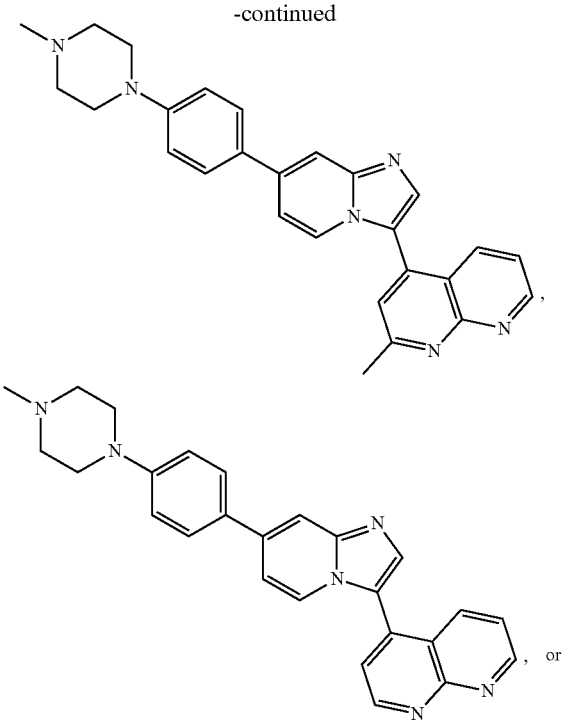

-continued

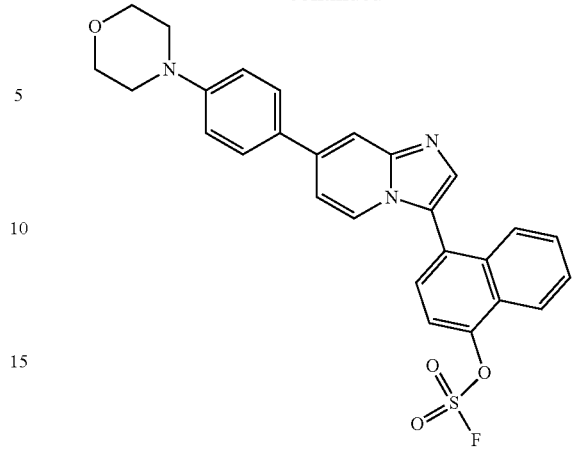

or a pharmaceutically acceptable salt thereof.

15. A pharmaceutical composition comprising a compound of claim 1 and a pharmaceutically acceptable carrier.

16. A pharmaceutical composition comprising a compound of claim 10 and a pharmaceutically acceptable carrier.

17. A pharmaceutical composition comprising a compound of claim 14 and a pharmaceutically acceptable carrier.

* * * * *

UNITED STATES PATENT AND TRADEMARK OFFICE
CERTIFICATE OF CORRECTION

PATENT NO. : 10,745,400 B2  
APPLICATION NO. : 16/353745  
DATED : August 18, 2020  
INVENTOR(S) : Hopkins et al.

Page 1 of 1

It is certified that error appears in the above-identified patent and that said Letters Patent is hereby corrected as shown below:

On the Title Page

Assignee:  
"Vanderbuilt University"  
Should be:  
--Vanderbilt University--.

Signed and Sealed this  
Seventeenth Day of November, 2020

Andrei Iancu  
*Director of the United States Patent and Trademark Office*